United States Patent
Kompella et al.

(10) Patent No.: US 9,765,072 B2
(45) Date of Patent: Sep. 19, 2017

(54) 1H-1,8-NAPHTHYRIDIN-2ONES AS ANTI PROLIFERATIVE COMPOUNDS

(71) Applicant: NATCO PHARMA LIMITED, Hyderabad (IN)

(72) Inventors: Amala Kompella, Hyderabad (IN); Venugopala Krishna Gampa, Hyderabad (IN); Srinivasulu Ganganamoni, Hyderabad (IN); Balakrishna Reddy Sirigireddy, Hyderabad (IN); Kali Satya Bhujanga Rao Adibhatla, Hyderabad (IN); Venkaiah Chowdary Nannapaneni, Hyderabad (IN)

(73) Assignee: NATCO PHARMA LIMITED, Hyderabad, IN (US)

( * ) Notice: Subject to any disclaimer, the term of this patent is extended or adjusted under 35 U.S.C. 154(b) by 0 days.

(21) Appl. No.: 15/316,832

(22) PCT Filed: Dec. 15, 2014

(86) PCT No.: PCT/IN2014/000777
§ 371 (c)(1),
(2) Date: Dec. 6, 2016

(87) PCT Pub. No.: WO2015/186137
PCT Pub. Date: Dec. 10, 2015

(65) Prior Publication Data
US 2017/0114057 A1    Apr. 27, 2017

(30) Foreign Application Priority Data
Jun. 6, 2014  (IN) .......................... 2781/CHE/2014

(51) Int. Cl.
C07D 471/04    (2006.01)

(52) U.S. Cl.
CPC .................. *C07D 471/04* (2013.01)

(58) Field of Classification Search
CPC .................................................. C07D 471/04
See application file for complete search history.

(56) References Cited

U.S. PATENT DOCUMENTS 8,114,874 B2    2/2012 Zou et al.
2013/0040949 A1    2/2013 Gray et al.

FOREIGN PATENT DOCUMENTS

WO    2007/075869 A2    5/2007
WO    2007/133560 A2    11/2007
WO    2008/046003 A2    4/2008

OTHER PUBLICATIONS

International Search Report for PCT/IN2014/000777 dated Mar. 31, 2015, 4 pages.
Deng, X et al., "Broad spectrum alkynyl inhibitors of T315I Bcr-Abl," Bioorganic & Medicinal Chemistry Letters 20 (2010) 4196-4200.
Huang, Wei-Sheng et al., "Discovery of 3-[2-(Imidazo[1,2-b]pyridazin-3-yl)ethynyl]-4-methyl-N-{4-[(4-methylpiperazin-1-yl)-methyl]-3-(trifluoromethyl)phenyl}benzamide (AP24534), a Potent, Orally Active Pan-Inhibitor of Breakpoint Cluster Region-Abelson (BCR-ABL) Kinase Including the T315I Gatekeeper Mutant ," J. Med. Chem. 2010, 53, 4701-4719.
O'Hare, Thomas et al., "AP24534, a Pan-BCR-ABL Inhibitor for Chronic Myeloid Leukemia, Potently Inhibits the T315I Mutant and Overcomes Mutation-Based Resistance," Cancer Cell. Nov. 6, 2009; 16(5): 401-412.
OECD/OCDE 420, OECD Guidelines for Testing of Chemicals, Adopted Dec. 17, 2001, 14 pages.
Zhou, Tianjun et al., "Structural Mechanism of the Pan-BCR-ABL Inhibitor Ponatinib (AP24534): Lessons for Overcoming Kinase Inhibitor Resistance," Chem Biol Drug Des 2011; 77: 1-11.

*Primary Examiner* — Golam M M Shameem
(74) *Attorney, Agent, or Firm* — Kilpatrick Townsend & Stockton LLP

(57) ABSTRACT

The present invention relates to novel antiproliferative 1H-1, 8-naphthyridin-2-ones of the general formula (I) or pharmaceutically acceptable salts thereof: In which the variable groups are as defined herein, and their preparation and use in therapeutic treatment of disorders related to inhibition of tyrosine kinases in warm blooded animals. The compounds can overcome imatinib induced drug resistance.

Formula (I)

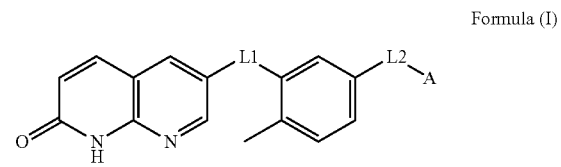

7 Claims, 7 Drawing Sheets

Anti-Invasive property of NRC-21T on Baf3/T315I Cell line (Establishment of Antagonism of NRC21T in T315I induced tumour in Nude Mice)

Fig. 5A
(Establishment of Antagonism of NRC21T in T315I induced tumour in nude mice, pictures of tumour)
Control
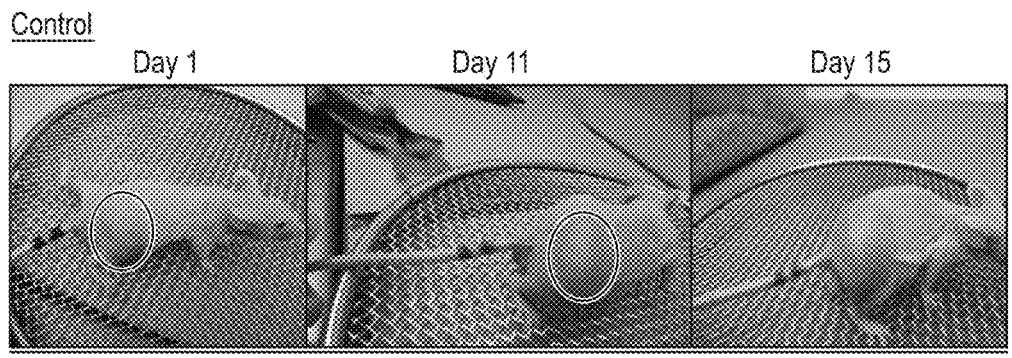
NRC21T
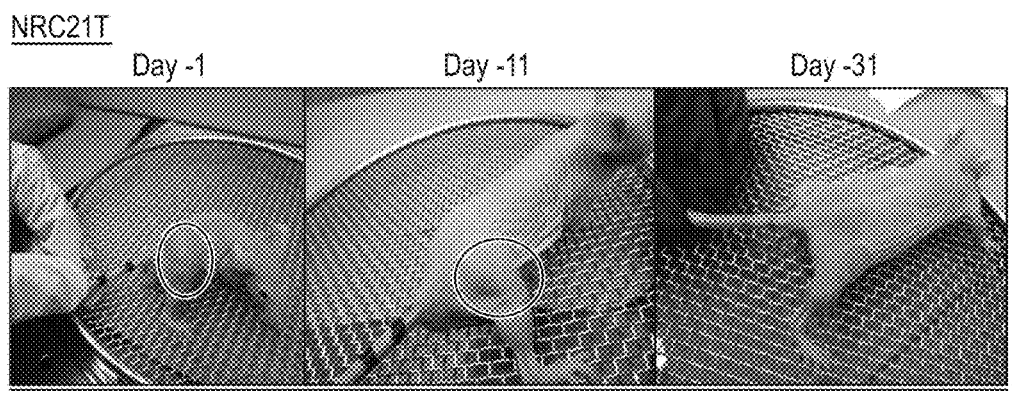
Ponatinib
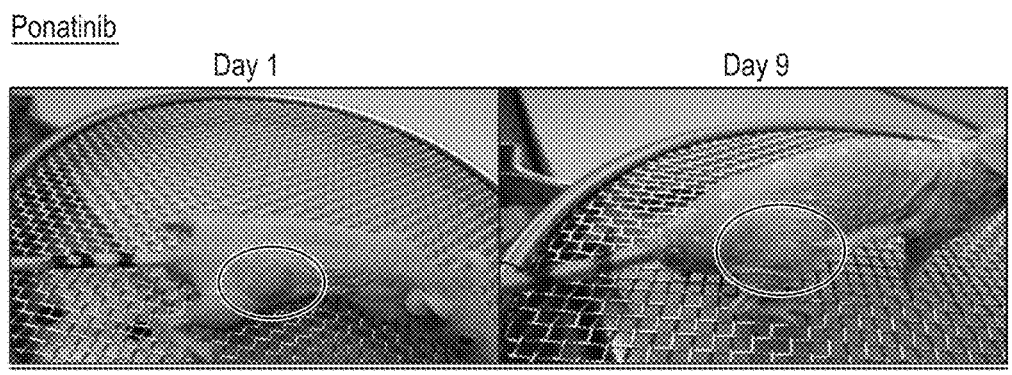

(Establishment of Antagonism of NRC21T in T315I induced tumour in nude mice, pictures of spleen)

(Survival time study)

(Pictures of spleen under survival time study)

1H-1,8-NAPHTHYRIDIN-2ONES AS ANTI PROLIFERATIVE COMPOUNDS

CROSS-REFERENCE TO RELATED APPLICATIONS

This application is a national phase application under 35 U.S.C. 371 claiming priority to PCT/IN2014/000777, filed Dec. 15, 2014, which application claims priority to IN 2781/CHE/2014, filed Jun. 6, 2014, the teachings of which are hereby incorporated by reference in their entireties for all purposes.

FIELD OF THE INVENTION

The present invention relates to novel antiproliferative 1H-1,8-naphthyridin-2-ones of the general formula (I) or pharmaceutically acceptable salts thereof:

Formual (I)

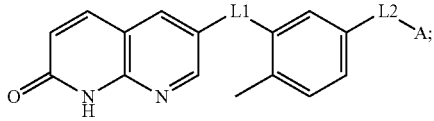

In which the variable groups are as defined herein, and their preparation and use in therapeutic treatment of disorders related to inhibition of tyrosine kinases in warm blooded animals.

BACKGROUND OF THE INVENTION

Protein tyrosine kinases are large family of proteins which plays a central role in the regulation of several disorders, particularly in the management of proliferative disorders. Deregulation of tyrosine kinase activity has emerged as a major mechanism by which cancer cells evade normal physiologic constraints on growth, proliferation and survival. An important mechanism leading to tyrosine kinase deregulation is mutation. Chronic myeloid leukaemia (CML) is a chronic myelodysplastic hematopoietic stem cell disorder syndrome. 95% of the CML are resulting from a reciprocal translocation between chromosome-9 and chromosome-22 of Philadelphia chromosome. Break point cluster region (BCR) sequences of chromosome-22 on translocation juxtaposes with the c-ABL tyrosine kinase of chromosome-9. The fusion gene produces a 210 KDa mutant protein in which the first exon of c-ABL has been replaced by BCR sequences, encoding either 927 or 902 amino acid. Another BCR-ABL fusion protein of 185 KDa containing BCR sequences from exon 1 fused to exon 2-11 of c-ABL, is found in 10% of adult ALL patients. The BCR-ABL chimeric gene product has a tyrosine kinase activity several fold higher than its normal counterpart and correlates with the disease phenotype.

Tyrosine kinase forms a significant share of all onco proteins taking a centre stage as possible targets for cancer therapy. The anticancer drug Gleevec/Glivec/Imatinib Mesylate (Novartis STI571) is a block buster drug for the treatment of CML and c-kit positive metastatic GIST. Gleevec selectively and effectively inhibits the kinase activity of BCR-ABL fusion protein, which is responsible for the constitutive proliferative signaling. While Imatinib is therapeutically highly effective, with improving prospects over time for sustained remission and potential to severely limit or eliminate disease progression and transformation, a good number of patients either fail or respond sub optimally to Imatinib. Disease eradication may not be possible with Imatinib.

Distinct patterns of resistance have evolved with the use of Imatinib, and Abl kinase mutations, which alter Imatinib binding or favour kinase conformations inaccessible to Imatinib, Dasatinib and Nilotinib the available alternate Abl kinase inhibitors and restore hematologic and cytogenetic remission in the majority of patients with primary failure or acquired resistance in chronic phase. In the advanced disease and Philadelphia chromosome (Ph)+ALL, responses are more limited and relapse is common.

ABL kinase mutations generally cluster into four main categories and are associated with particular numbered amino acid residues: ATP binding loop (p-loop), particularly Y253 and E255 mutants; T315 mutants; M351 mutants; and activation loop (a-loop), particularly H396 mutants. Modelling of Imatinib and other kinase inhibitors with the crystal structure of the catalytic region of the ABL kinase suggests that mutations may interrupt critical drug contact points or induce or favour a conformation of the Abl kinase in which drug binding is reduced or precluded. Now termed the "gatekeeper" position, mutations at threonine 315 confer resistance both to Imatinib and "second generation" Abl kinase inhibitors Nilotinib and Dasatinib.

Thus there is an unmet need with regard to treatment of patients having the T315I mutation. Omacetaxine (homo-harringtonine) is approved by FDA for the treatment of adult patients with chronic or accelerated phase chronic myeloid leukemia (CML) with resistance and/or intolerance to two or more tyrosine kinase inhibitors (TKIs). However, it is administered subcutaneously with non-specific mechanism of action. Other drug candidates include rebastinib (WO 2008/046003) and the Ponatinib (WO 2007/075869). Ponatinib (ICLUSIG) is an approved as oral drug candidate and it is developed by Ariad pharmaceuticals for the treatment of chronic myeloid leukemia (CML) and Philadelphia chromosome-positive (Ph+) acute lymphoblastic leukemia (ALL). Ponatinib was intended to target not only native BCR-ABL, but also its isoforms that carry mutations that confer resistance to treatment with existing tyrosine kinase inhibitors, including especially the T315I mutation for which no effective therapy exists. However the Food and Drug Administration temporarily suspended sales of the drug in the U.S. in 2013 because of "the risk of life-threatening blood clots and severe narrowing of blood vessels". This suspension was partially lifted subsequently with revised prescribing information, a new "Black Box Warning" and a "Risk Evaluation and Mitigation Strategy" in place.

Thus there is a need for newer selective tyrosine kinase inhibitors which are orally active, safer than existing therapies particularly with regard to decrease in risk of life-threatening blood clots and severe narrowing of blood vessels and efficacious against the kinase mutations, including the T315I mutant. The present invention relates to a new family of 1H-1,8-naphthyridin-2-ones which are potent inhibitors of Abl tyrosine kinase and their mutated forms, including the T315I mutant. The compounds of the present invention are devoid of some of the short comings of the existing drug products.

BRIEF DESCRIPTION OF THE DRAWINGS

FIG. 5A shows Establishment of Antagonism of NRC21T in T315I induced tumour in nude mice, pictures of tumour

DETAILED DESCRIPTION OF THE INVENTION

Figure 1:
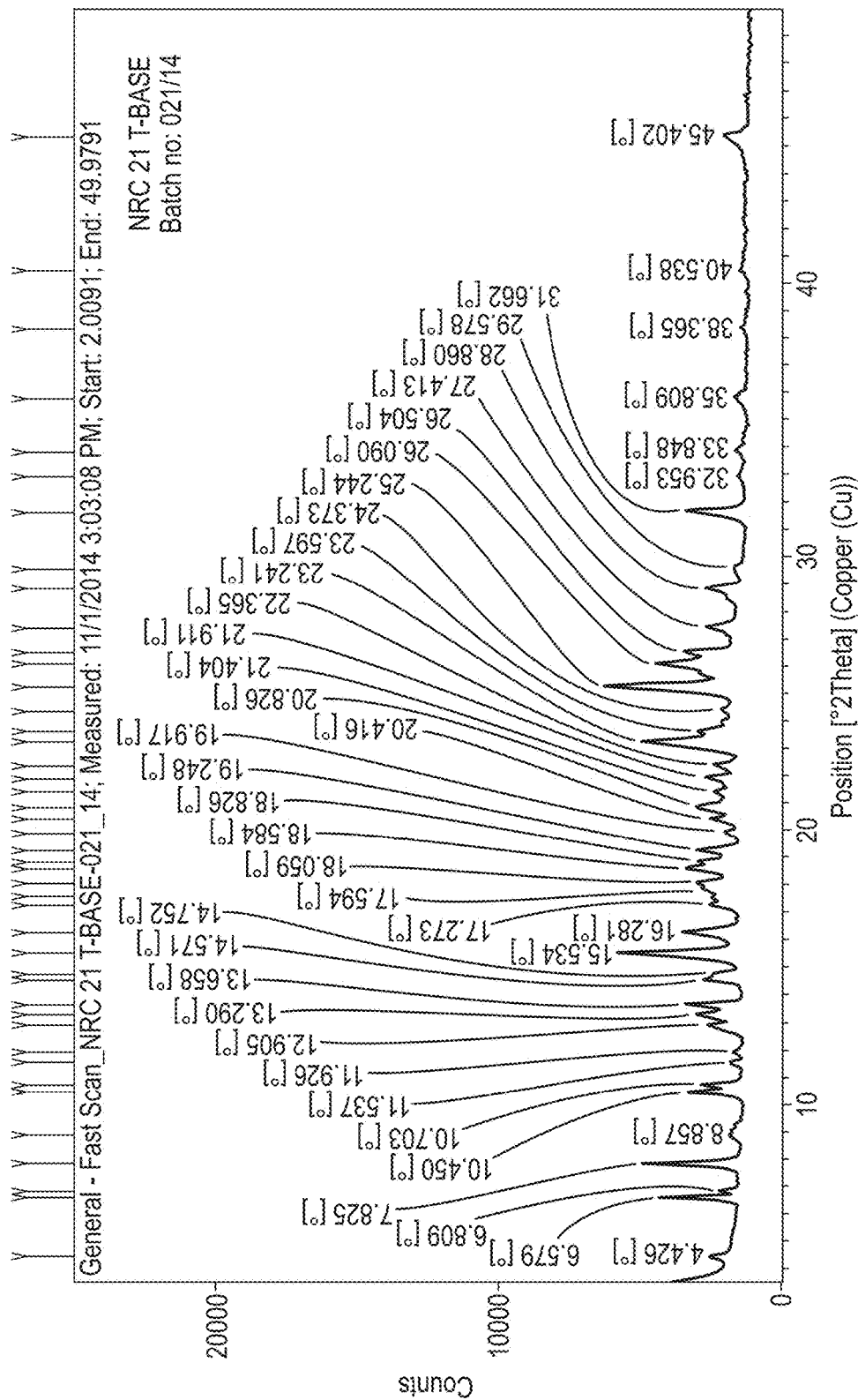
FIG. 1 shows x-ray powder diffraction patterns (XRPDs) for NRC 21T

The present invention relates to a compound of formula (I)

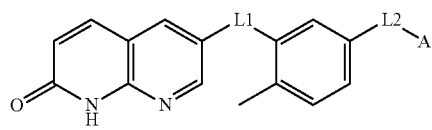

Formula (I)

or a pharmaceutically acceptable salts thereof; wherein,

L1 is Linker selected from unsaturated carbon bond; preferably carbon-carbon triple bond or carbon-carbon double bond;

L2 is a linker selected from NHC(O)—, C(O)NH—;

Ring A includes, but are not limited to substituted 5 or 6 membered aryl or heteroaryl ring.

Illustrative examples of ring A groups include:

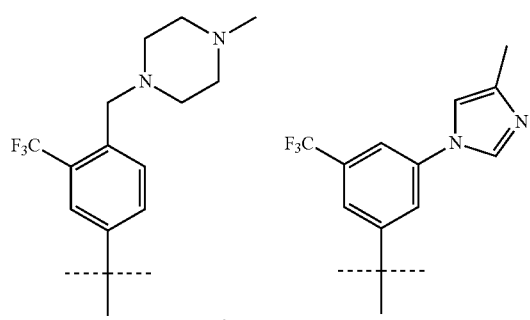

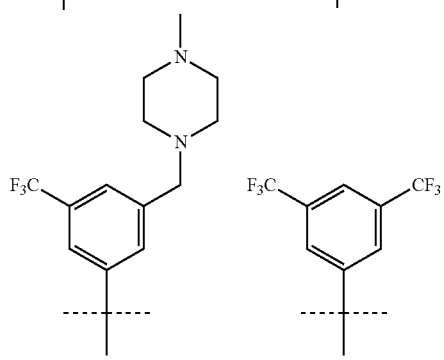

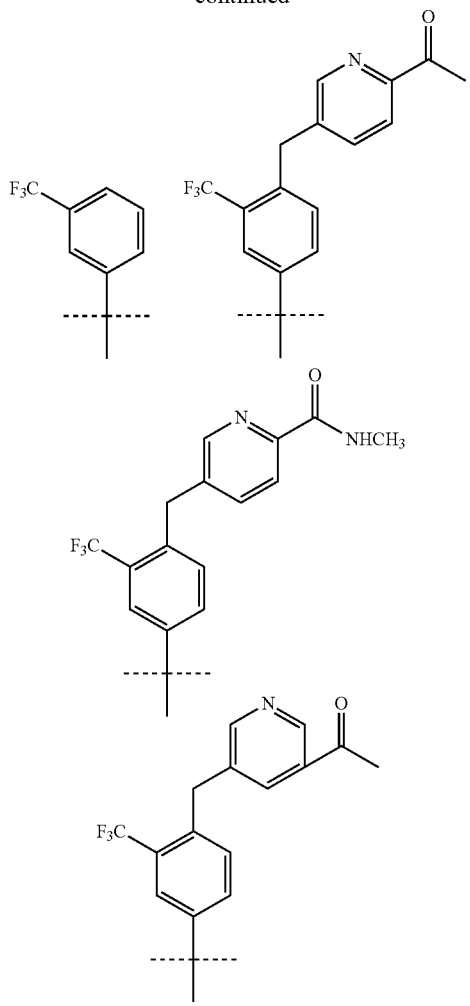

Non limiting examples of compound of formula (I) includes but are not limited to having the following structures:

Compounds of formula I (a-u)

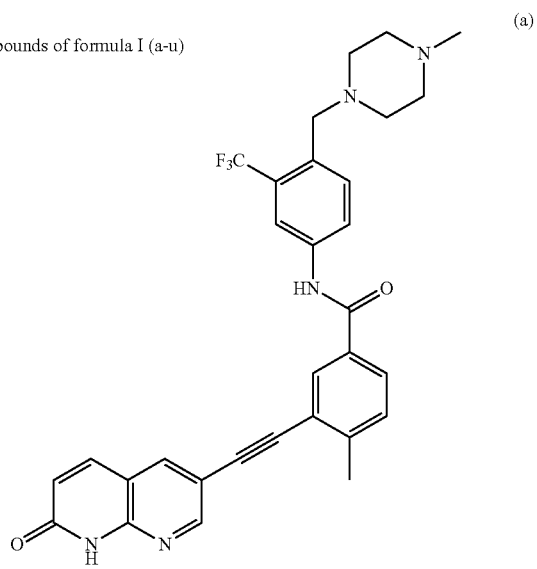

(a)

-continued
(b)
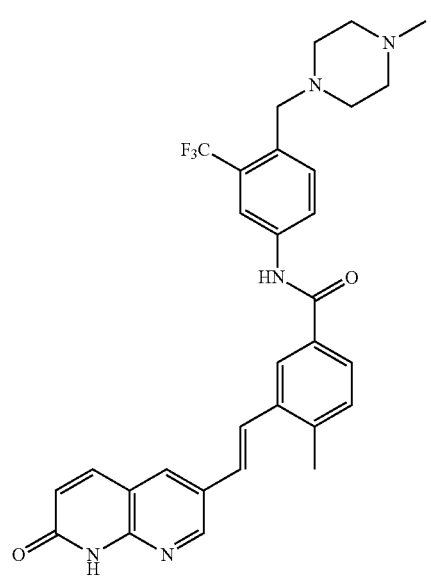
(c)
(d)
-continued
(e)
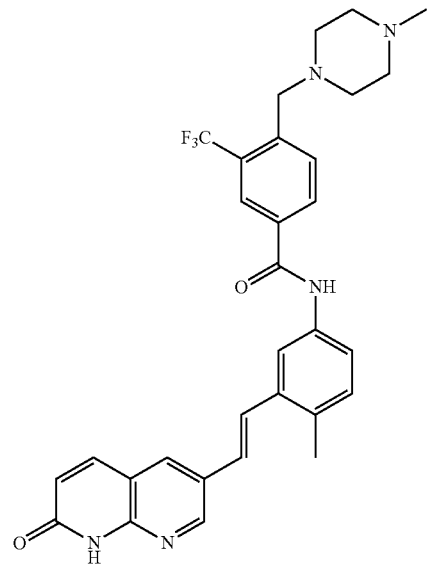
(f)
(g)

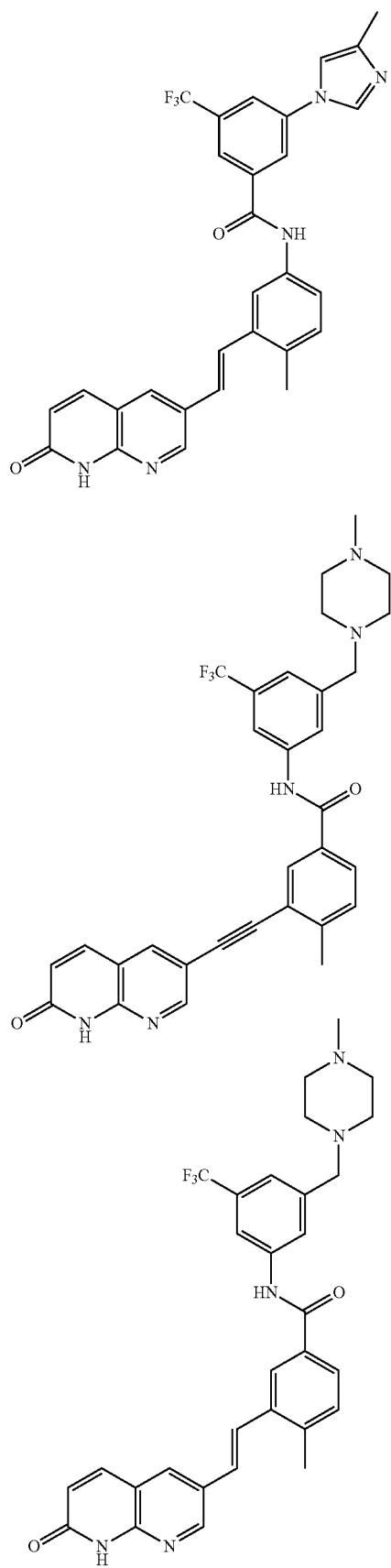
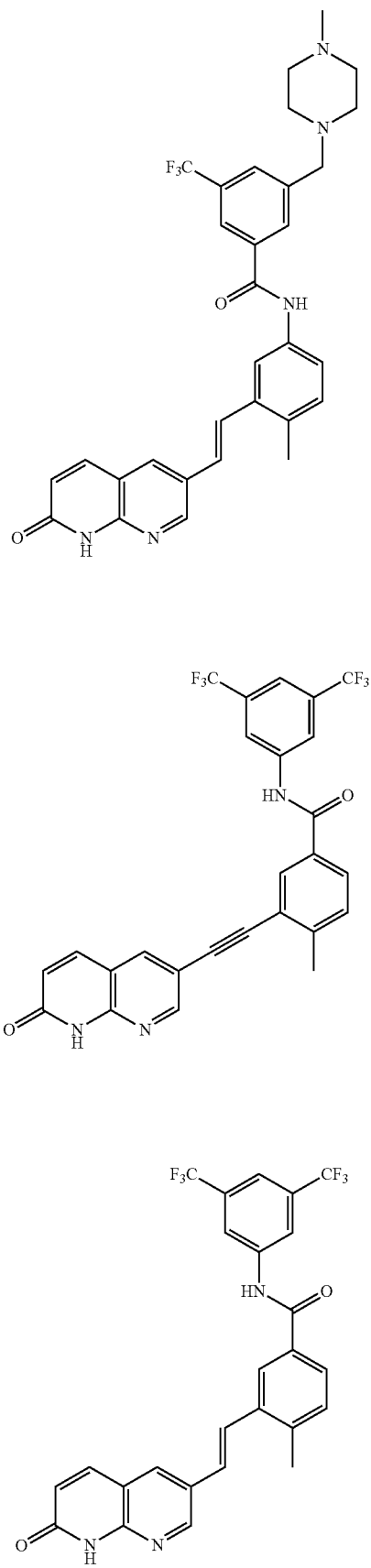

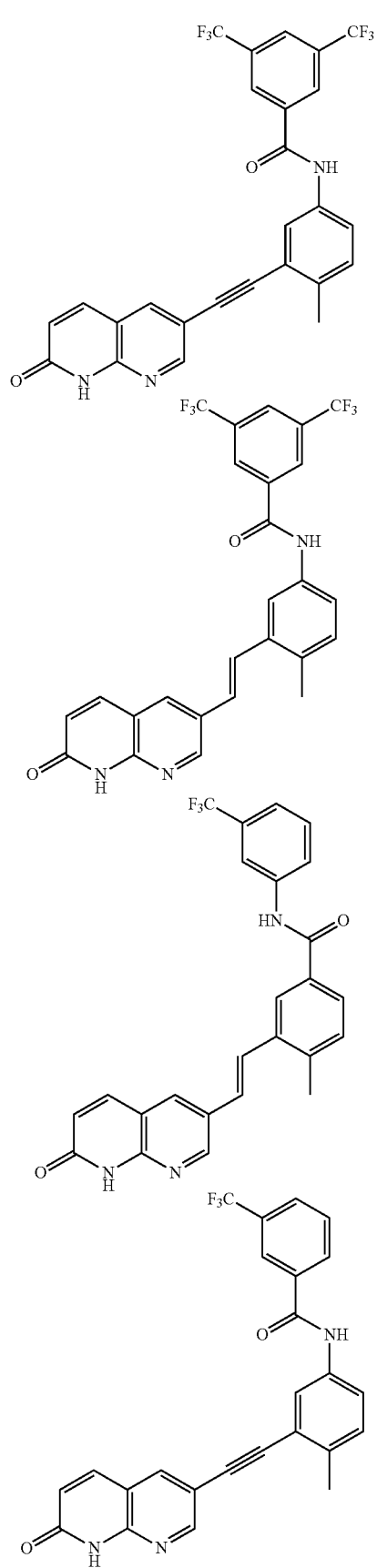
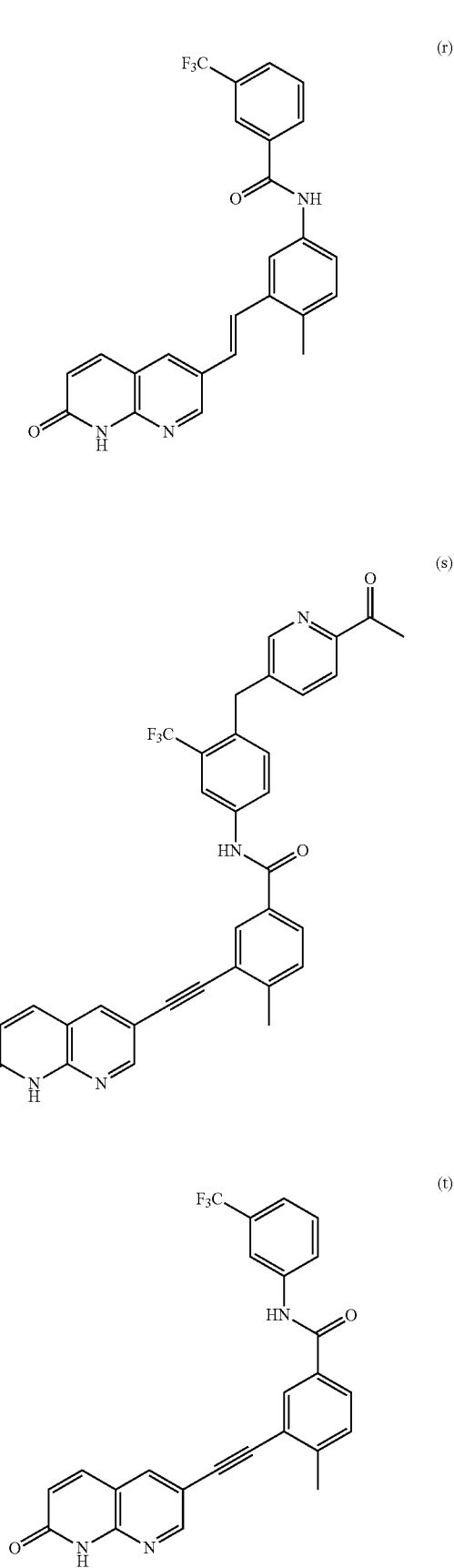

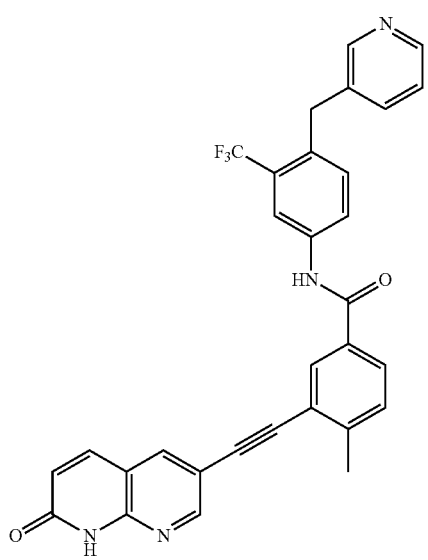

(u)

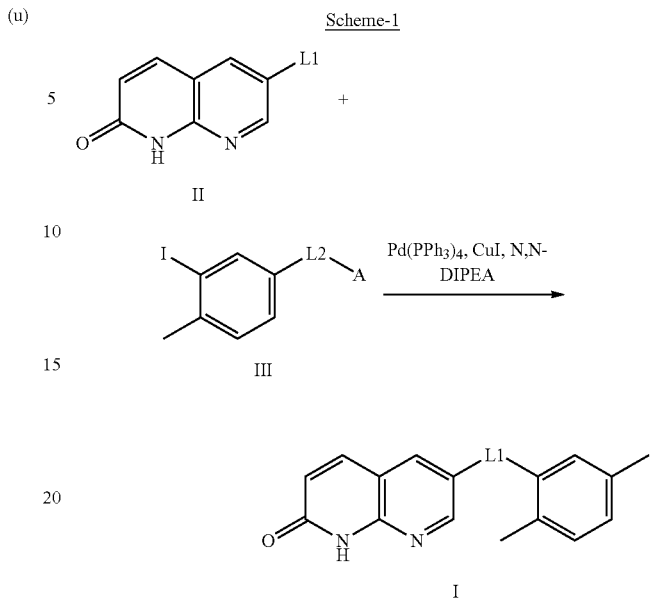

Scheme-1

The present invention provides a process for the preparation of compounds of formula (I) by palladium catalyzed Sonogashira coupling of 6-substituted naphthyridin-2-ones (II) with iodobenzamides (III). The schematic representation is as follows:

Several illustrative overall synthetic approaches to the preparation of two key intermediates II and III, based on known transformations, are illustrated in schemes 2 to 5.

Scheme-2: Represents preparation of intermediates-II: (First set)

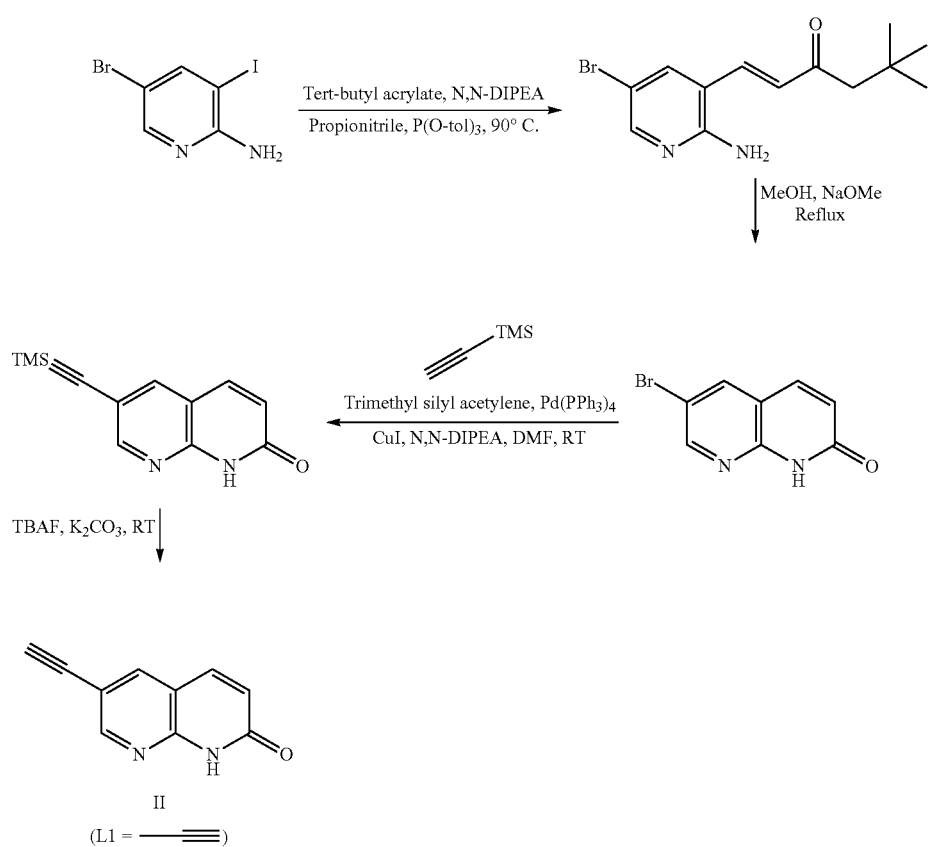

Scheme-3: Represents preparation of intermediates-II: (Second set)

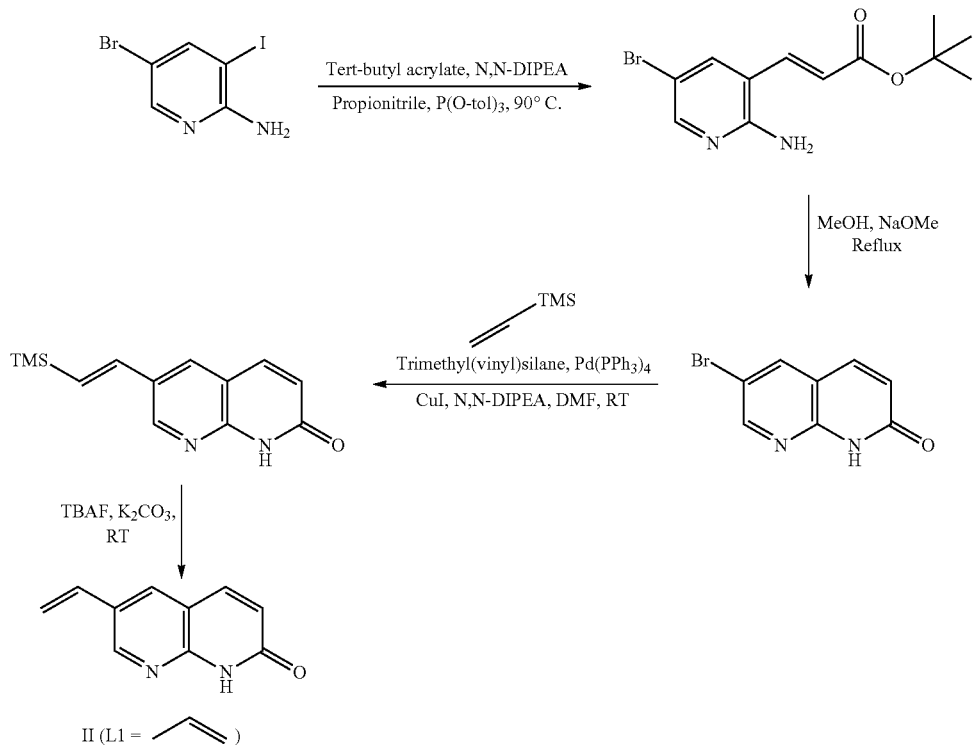

Scheme-4: Represents preparation of intermediate-III and compound of formula (I)

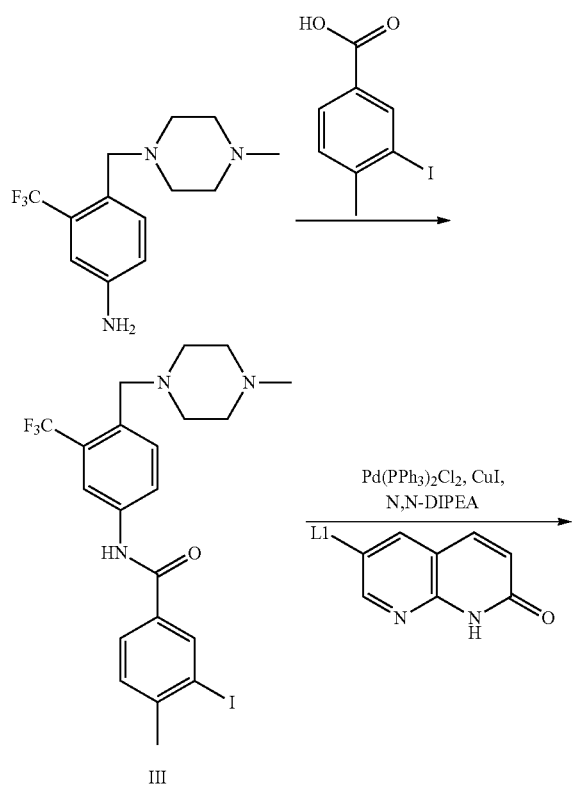

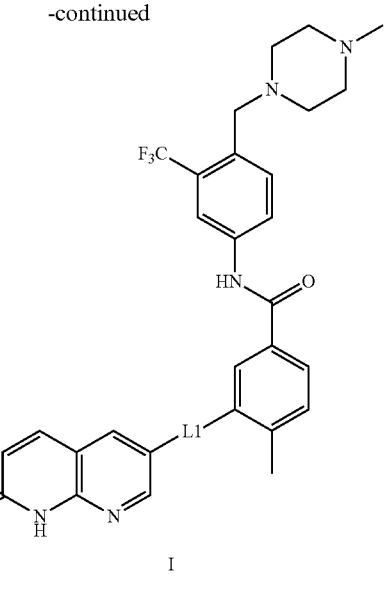

Compound of formula (I) can be prepared as per above schemes. Compound of formula (I) can be converted into an N-oxides, or its pharmaceutically acceptable salts. For example, suitable inorganic acids are, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, oxalic acid, amino acids, such as arginine or lysine, maleic acid, hydroxymaleic acid, methylmaleic acid, cyclohexanecarboxylic acid, adamantanecarboxylic acid, benzoic acid, -phenoxy benzoic acid, 2-acetoxy benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3-or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The compounds of the formula (I) or N-oxide or pharmaceutically acceptable salts thereof inhibit to varying degrees the receptor and non-receptor tyrosine kinases of all, which play a role in growth regulation and transformation in mammalian cells, including human cells. The receptor tyrosine kinases may be kinases of the EGF family, e.g. ErbB2 kinase (HER-2), ErbB3 kinase, ErbB4 kinase; insulin-like growth factor receptor kinase (IGF-1 kinase), especially members of the PDGF-receptor tyrosine kinase family, such as PDGF-α and PDGF-β receptor kinase, JAK-2, CSF-1-receptor kinase, Phosphatidylinositol 3-kinases (PI-3-kinases or PI3Ks), AKT, CDK, mTOR, Kit-receptor kinase, Flt-3, Flt-4, FGFR-1, FGFR-3, FGFR-4, c-Met, RON, c-Ret, ALK and VEGF-receptor kinase. The non-receptor tyrosine kinases may be kinases such as Abl/Bcr-abl Kinase, Arg, kinases from the Src family, c-Src kinase, c-Yes. Lck, Lyn and Fyn. The compounds of the present invention have been found to inhibit especially Abl/Bcr-Abl kinase, including mutant forms; Lyn and Lck kinases. The compounds of the formula (I) or N-oxide or pharmaceutically acceptable salts thereof inhibit to varying degrees the mutant forms of Abl/Bcr-Abl kinase which include the mutants of the P-loop of the kinase i.e., L284V, G250E, Q225H, Y253F & E255K; the C-helix mutants of the kinase i.e., D276G and E279H; The ATP binding region mutants of the kinase i.e., V299L, T315I and F317L; SH2-contact mutant of the kinase i.e., M351T; substrate binding region mutant of the kinase i.e., F359V; the A-loop mutants of the kinase i.e., L384M, H395P, H396R and G398R; and the C-terminal lobe mutant kinase i.e., F486S.

The compounds of the present invention have been found to inhibit especially the important mutants of abl/Bcr-Abl kinases i.e., Q252H, Y253F, M351T, H396P and more particularly the compounds of formula (I) inhibit the highly resistant form of the mutated kinase i.e., the T315I mutant.

The compounds of the present invention relates furthermore to a method for the treatment of a neoplastic disease or disorders dependent on tyrosine kinases especially chronic myelogenous leukemia (CML), chronic lymphocytic leukemia (CLL), acute lymphoblastic leukemia (ALL), acute myeloid leukemia (AML), myelodysplastic syndrome, melanoma, germ cell tumours, gastrointestinal stromal tumour (GIST), non-small cell lung cancer (NSCLC), mastocytosis, neuroblastoma, glioblastoma, astrocytoma, hepatocellular carcinoma, renal cell cancer, breast cancer, cutaneous systemic sclerosis, prostate and colorectal cancer and other solid tumours, diabetes remissions.

The present invention relates furthermore to a method for the treatment of a neoplastic disease which responds to an inhibition of a protein kinase activity, which comprises administering a compound of formula (I) or a N-oxide or a pharmaceutically acceptable salt thereof, in a quantity effective against said disease, to a warm-blooded animal requiring such treatment.

In particular the present invention relates to a method of treatment of proliferative disorders especially leukemia, irrespective of etiology of the disorder, which respond to inhibition of the aforementioned tyrosine kinases, particularly the Abl/Bcr-Abl tyrosine kinase and one or more of its severe mutated forms. The treatment comprises administering a compound of formula (I) or an N-oxide or a pharmaceutically acceptable salt thereof, in a quantity effective against said disease, to a warm-blooded animal requiring such treatment.

The biological efficacy of the compounds of the present invention has been established by In vitro efficacy evaluation on BCR-abl positive cell line K562 and mutant cell lines Baf3/T315i, M351T, E255K and WT; Matrigel invasion assay; Determination of MTD of NRC21T; Establishment of Antagonism of NRC21T in T315I induced tumour in Nude Mice; Establishment of Survival time of NRC21T in SCID Mice.

On the basis of these studies, the compounds of formula (I) according to the present invention shows therapeutic efficacy especially against disorders dependent on TK, especially in proliferative diseases.

The present invention also relates to pharmaceutical compositions comprising an affective amount of compound of formula (I) or a N-oxide or a pharmaceutically acceptable salt especially an amount effective in the prevention or therapy of one of the above mentioned diseases, of the active ingredient together with pharmaceutically acceptable carriers that are suitable for topical, enteral, for example oral or rectal, or parental administration, and may be inorganic or organic, solid or liquid. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g.

Eudragit®), potassium chloride, powdered cellulose, sodium chloride, sorbitol and talc.

Solid pharmaceutical compositions that are compacted into a dosage form, such as capsules may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a capsule is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavouring agents and flavor enhancers for pharmaceutical products that may be included in the composition of the present invention include maltol, vanillin, ethyl vanillin, menthol, citric acid, fumaric acid, ethyl maltol, and tartaric acid. Solid compositions may also be dyed using any pharmaceutically acceptable colorant to improve their appearance and/or facilitate patient identification.

The details of the present invention are provided in the Examples given below which are provided for illustrative purposes only and are not intended to limit the scope of the invention in any way.

EXPERIMENTAL SECTION

Example-1

4-Methyl-N-[4-[(4-methylpiperazin-1-yl) methyl]-3-(trifluoromethyl) phenyl]-3-[2-(7-oxo-8H-1,8-naphthyridin-3-yl) ethynyl]benzamide (Development code: NRC21T)

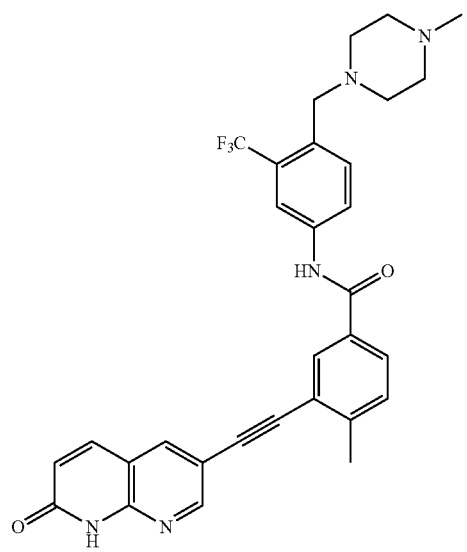 [SMILES: Cc1ccc(C(=O)Nc2ccc(CN3CCN(C)CC3)c(C(F)(F)F)c2)cc1C#Cc1cnc2[nH]c(=O)ccc2c1]

1.1 2-Amino-5-bromo-3-iodo pyridine

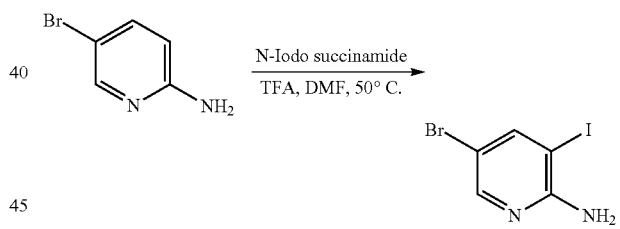

To a solution of 2-amino-5-bromo pyridine in DMF, trifluoro acetic acid (1.1 equiv) was added at room temperature, followed by addition of N-Iodo succinimide (1.1 equiv) and the reaction mixture was heated at 50° C. for 180 min. After completion of the reaction, reaction mass was cooled to room temperature and the product was precipitated by adding the reaction mixture to water. After neutralization with sodium thiosulfate and 1N NaOH the title compound was collected by filtration as a brown solid with 90% yield.

1.2 (E)-tert-butyl 3-(2-amino-5-bromopyridin-3-yl) acrylate

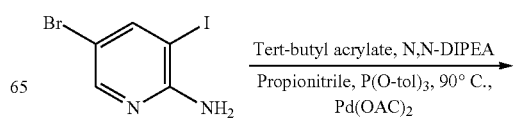

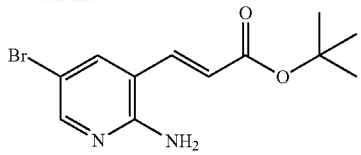

To a 2-amino-5-bromo-3-iodo pyridine (1 equiv), tert-butyl acrylate (2 equiv), and isopropanol (2 equivalents), Ethyl nitrite (3 equiv) was added propionitrile (10 equiv) and then DMF (10 equiv). The solution was de-oxygenated with nitrogen gas for 15 minutes. The mixture was treated with Pd(OAc)2 (0.1 equiv) and P(O-tol)3 (0.2 equiv) then heated to 90° C. for 16 h then filtered through a pad of silica gel. The filtrate was concentrated, diluted with water, extracted with ethyl acetate and the organic layer was concentrated under vacuum below 60° C. The compound was collected by filtration using hexane as solvent (70% yield). ESI MS m/z 299 (100%).

1.3 6-Bromo-1H-1,8-naphthyridin-2-one

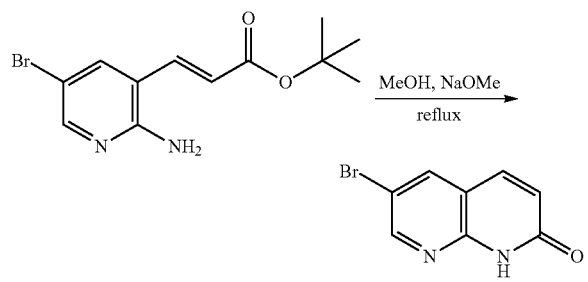

To a solution of (E)-tert-butyl 3-(2-amino-5-bromopyridin-3-yl) acrylate (1 equiv) in anhydrous methanol was treated with sodium methoxide (4.9M, 5 equiv) under nitrogen gas atmosphere. The solution was heated at reflux temperature for 3 h then cooled to room temperature. The mixture was cooled in an ice water bath and treated with water under rapid stirring to give a precipitate. The solid was filtered and washed with water. Dried under reduced pressure to give an off-white solid (80% yield). ESI MS m/z 225 (100%).

1.4 6-(2-Trimethylsilylethynyl)-1H-1,8-naphthyridin-2-one

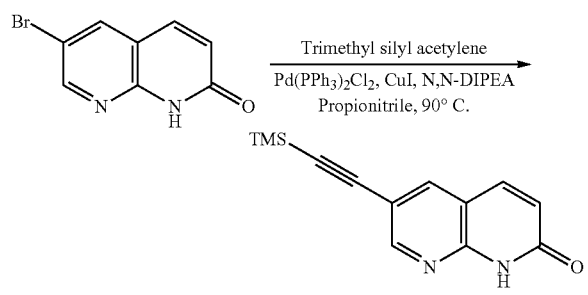

A mixture of 6-bromo-1H-1,8-naphthyridin-2-one (1 equiv), Pd(PPh₃)₂Cl2 (0.1 equiv), CuI (0.15 equiv), (i-Pr)₂EtN (4 equiv) in propionitrile was deoxygenated with nitrogen gas for 15 minutes. Then trimethyl silyl acetylene (2 equiv) was added and heated to 90° C. for 10 h. After reaction mass was filtered through a pad of silica gel at room temperature. The filtrate was concentrated and the compound was collected by filtration using propionitrile solvent at 0-5° C. (60% yield).

1.5 6-Ethynyl-1H-1,8-naphthyridin-2-one

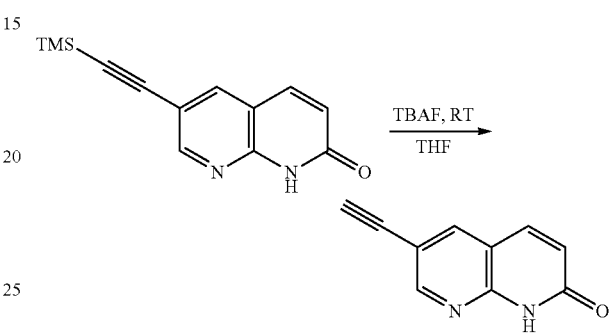

To a solution of 6-(2-trimethylsilylethynyl)-1H-1,8-naphthyridin-2-one (1 equiv) in THF (10times) was slowly added 1M TBAF solution in THF (1.1 equiv) at room temperature under nitrogen gas atmosphere for 15 minutes and stirred for 15 minutes. Product formation was observed by quenching the reaction mass in to the water. Product was collected by filtration at 0-5° C. For further purification, recrystallization was done in acetone solvent (80% yield).

1.6 4-Nitro-2-(trifluoromethyl) benzoic acid (SC1)

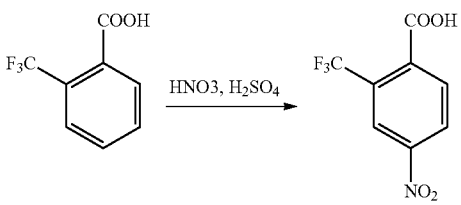 [SMILES: O=C(O)c1ccccc1C(F)(F)F ; O=C(O)c1ccc([N+](=O)[O-])cc1C(F)(F)F]

Under Nitrogen gas atmosphere, a mechanically stirred mixture of 2-trifluoromethyl benzoic acid (1 equiv) and Conc.H₂SO₄ (22 equiv) was cooled in an ice bath to 0-5° C. Then fuming nitric acid (9.8 equiv) was added drop wise at 0-5° C. for 60 min. The ice bath was removed and stirring continued for 120 min at room temperature. After completion of reaction the reaction mixture was poured into ice water, stirred for 60 min at room temperature. Filtered the suspension, washed with chilled water and obtained the crude title compound. To remove the regio isomer the crude product was crystallized from water (45% yield). M.P: 137-142° C.

1.7 (4-Methylpiperazin-1-yl)-[4-nitro-2-(trifluoromethyl) phenyl]methanone (SC2)

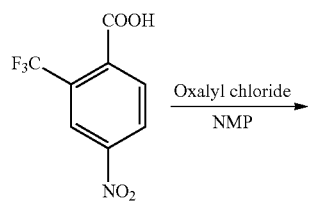

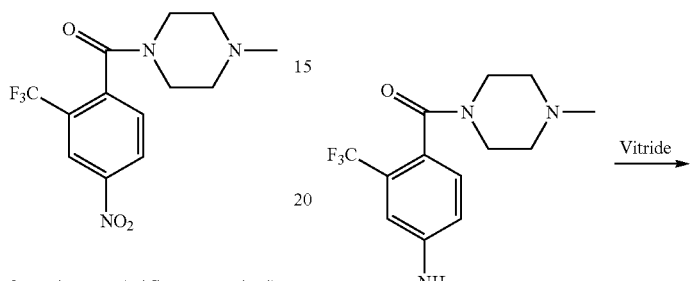

To an ice-cooled solution of 4-nitro-2-(trifluoromethyl) benzoic acid (1 equiv), CH$_2$Cl$_2$ (15times) and DMF (0.5 equiv) under nitrogen atmosphere, oxalylchloride (2 equiv) was added drop wise. After 4 hrs, the resulting solution was concentrated in vacuum. The residue was dissolved in CH$_2$Cl$_2$ and added drop wise to an ice cooled solution of N-methyl piperazine (2.1 equiv) in CH$_2$Cl$_2$. After stirring for 3 h, the mixture was diluted with CH$_2$Cl$_2$ and washed with water, 3 portions of 10% solution of Na$_2$CO$_3$, water and brine. The organic phase was concentrated to get the title compound as an oil (96% yield).

1.8 [4-Amino-2-(trifluoromethyl) phenyl]-(4-methylpiperazin-1-yl)methanone (SC3)

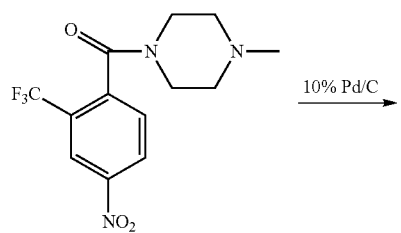

To a solution of (4-methylpiperazin-1-yl)-[4-nitro-2-(trifluoromethyl) phenyl]methanone (1 equiv) in methanol (3 times) was added 10% Pd/C under nitrogen atmosphere. Then slowly added 66% aq. ammonium formate solution (5 equiv) at room temperature (Exothermic). After stirring for 120 min, filtered through a pad of silica gel. The filtrate was concentrated and diluted with water, extracted with CH$_2$Cl$_2$ and washed with water. After CH$_2$Cl$_2$ concentration compound was collected by filtration using hexane solvent (90% yield).

1.9 4-[(4-Methylpiperazin-1-yl) methyl]-3-(trifluoromethyl) aniline (SC4)

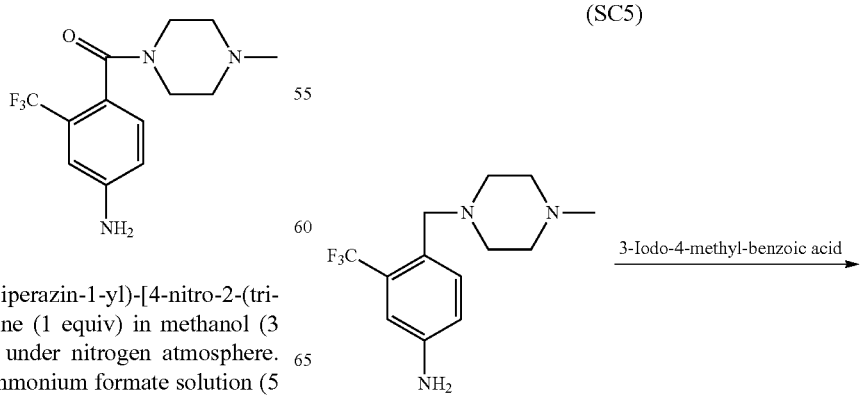

To a solution of vitride (3 equiv) in toluene (6times) under nitrogen atmosphere was slowly added lot wise [4-amino-2-(trifluoromethyl) phenyl]-(4-methylpiperazin-1-yl)methanone (1 equiv) at room temperature during 2 h (exothermic). After stirring for 4 h at 65° C., slowly added 8% aq. NaOH solution (12 equiv) during 1 h at room temperature. Resulting solution was stirred for 30 minutes, extracted with toluene, combined toluene layers were dried over Na$_2$SO$_4$ and concentrated. Crystallization form boiling hexane afforded the title compound (50% yield).

1.10 3-iodo-4-methyl-N-[4-[(4-methylpiperazin-1-yl) methyl]-3-(trifluoromethyl) phenyl] benzamide (SC5)

-continued

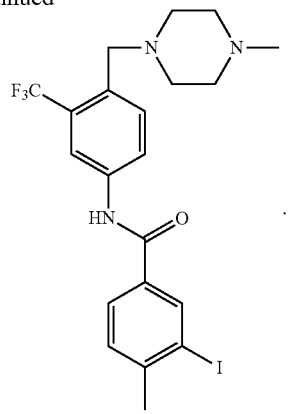

To a solution of 4-[(4-methylpiperazin-1-yl)methyl]-3-(trifluoromethyl)aniline (0.7 equiv) in THF (4times) under nitrogen atmosphere was added 3-Iodo-4-methyl benzoyl chloride (1 equiv, prepared from the reaction of 3-iodo-4-methylbenzoic acid and $SOCl_2$) in THF at room temperature for 30 minutes followed by drop wise addition of (i-Pr)$_2$EtN (2 equiv) and 4-DMAP (0.2 equiv). After stirring at ambient temperature for 120 min, the reaction mixture was quenched with water, extracted with ethyl acetate. After drying over $Na_2SO_4$, concentrated the ethyl acetate layer to provide the crude product. Acetone was added to this crude product and was converted to HCl salt using IPA-HCl (85% yield).

1.11 4-Methyl-N-[4-[(4-methylpiperazin-1-yl) methyl]-3-(trifluoromethyl) phenyl]-3-[2-(7-oxo-8H-1,8-naphthyridin-3-yl) ethynyl]benzamide (Development code: NRC21T)

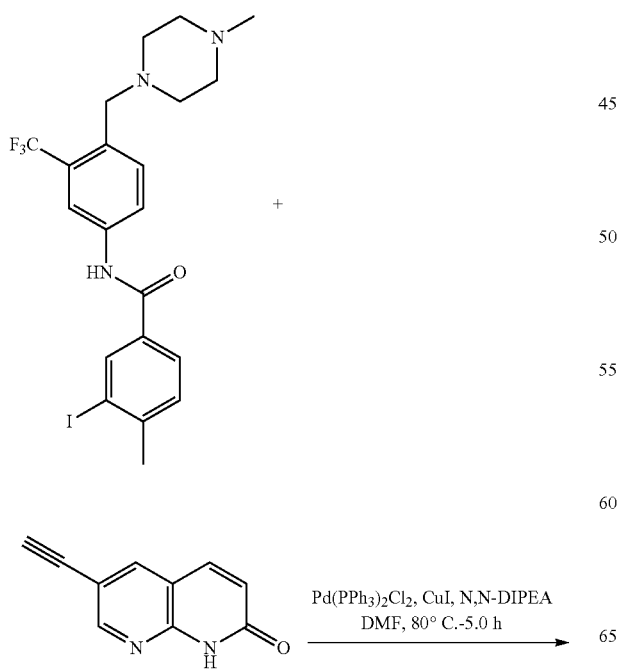

-continued

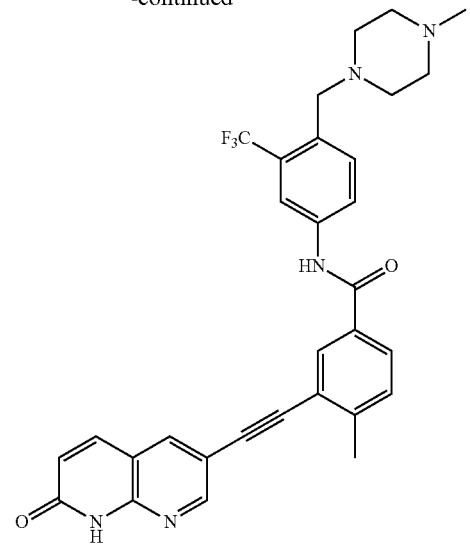

Figure 2:
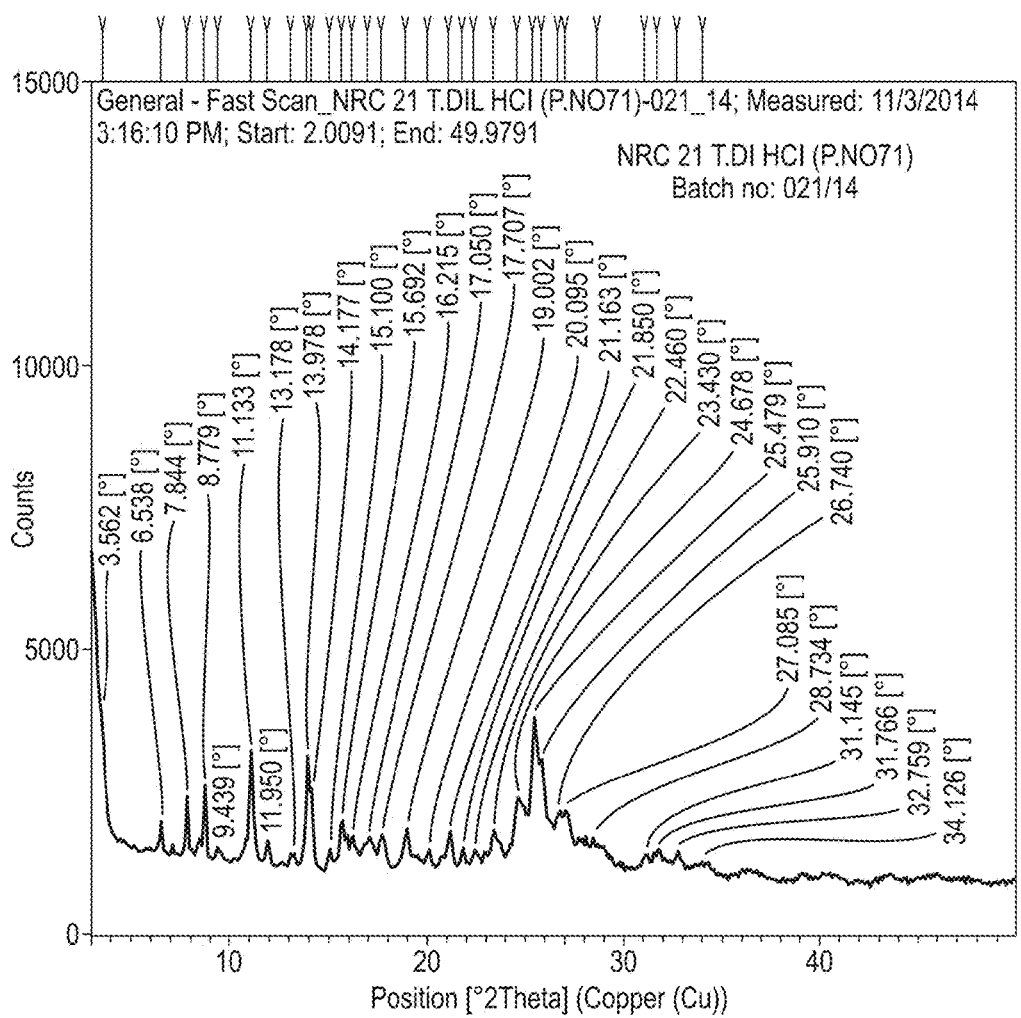
FIG. 2 shows x-ray powder diffraction patterns (XRPDs) for NRC 21T hydrochloride salt

A mixture of 3-Iodo-4-methyl-N-[4-[(4-methylpiperazin-1-yl)methyl]-3-(trifluoromethyl) phenyl]benzamide (0.8 equiv, prepared as per 1, SC5), 6-ethynyl-1H-1,8-naphthyridin-2-one (1 equiv, prepared as per 1.5), Pd(PPh3)$_2$Cl$_2$ (0.1 equiv), CuI (0.15 equiv), (i-Pr)$_2$EtN (4 equiv), in DMF under nitrogen atmosphere was deoxygenated with Nitrogen gas for 30 minutes. Reaction mass was heated to 80° C. for 5 h. Filtered through a pad of silica gel at room temperature and filtrate was concentrated, diluted with water and methanol (1:2 mixture). The compound was collected by filtration and dried. The XRD is depicted in FIG. 1. The compound was subjected to salt formation with conc. HCl in methanol medium to yield titled compound as hydrated dihydrochloride salt (70% yield). The XRD is depicted in FIG. 2.

$^1$HNMR (400 MHz, DMSOD$_6$) δ12.430 (s, 1H), 10.678 (s, 1H), 8.742 (s, 1H), 8.397 (s, 1H), 8.288 (s, 1H), 8.156 (d, 2H), 7.958 (d, 2H), 7.893 (s, 1H), 7.537 (d, 1H), 6.645 (d, 1H), 3.946 (bs, 2H), 3.169-3.474 (bs, 8H), 2.794 (s, 3H), 2.586 (s, 3H). ESI MS m/z −560.3(M+H)$^+$.

Example-2

4-Methyl-N-[4-[(4-methylpiperazin-1-yl) methyl]-3-(trifluoromethyl) phenyl]-3-[(E)-2-(7-oxo-8H-1,8-naphthyridin-3-yl) vinyl] benzamide (Development code: NRC20T)

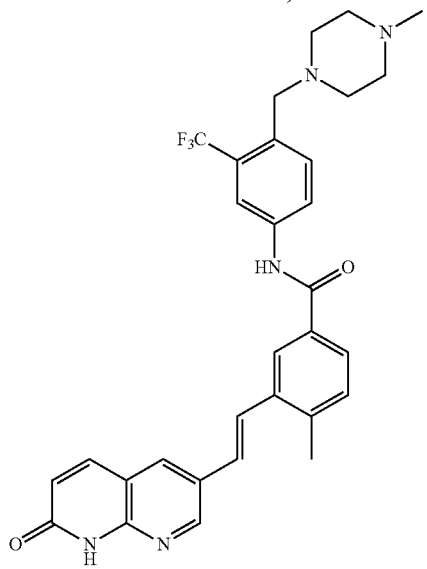

2.1 6-[2-Trimethylsilylvinyl]-1H-1,8-naphthyridin-2-one

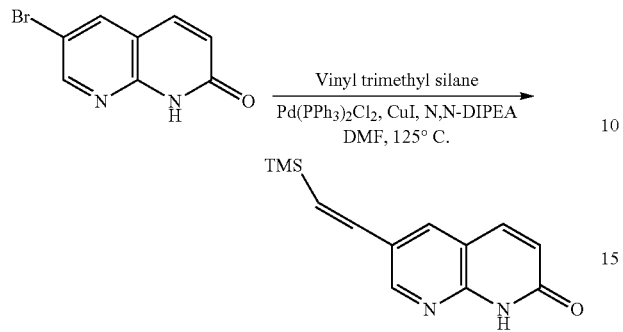

A mixture of 6-bromo-1H-1,8-naphthyridin-2-one (1 equiv, which was prepared as per prepared as per-1.3), Pd(PPh$_3$)$_2$Cl$_2$ (0.1 equiv), CuI (0.15 equiv), (i-Pr)$_2$EtN (4 equiv) in DMF (15 times) was deoxygenated with nitrogen for 15 minutes. Then vinyl trimethyl silane (2 equiv) was added and heated to 125° C. for 10 h. The reaction was monitored by thin layer chromatography. Filtered through a pad of silica gel at room temperature. The filtrate was concentrated and the residue was purified by silica gel chromatography (eluted with 20 to 30% ethyl acetate/hexane) to provide the title compound as a solid (30% yield). ESI MS m/z −245.22(M+H)$^+$.

2.2 4-Methyl-N-[4-[(4-methylpiperazin-1-yl)methyl]-3-(trifluoromethyl) phenyl]-3-[(E)-2-(7-oxo-8H-1,8-naphthyridin-3-yl) vinyl] benzamide (Development code: NRC20T)

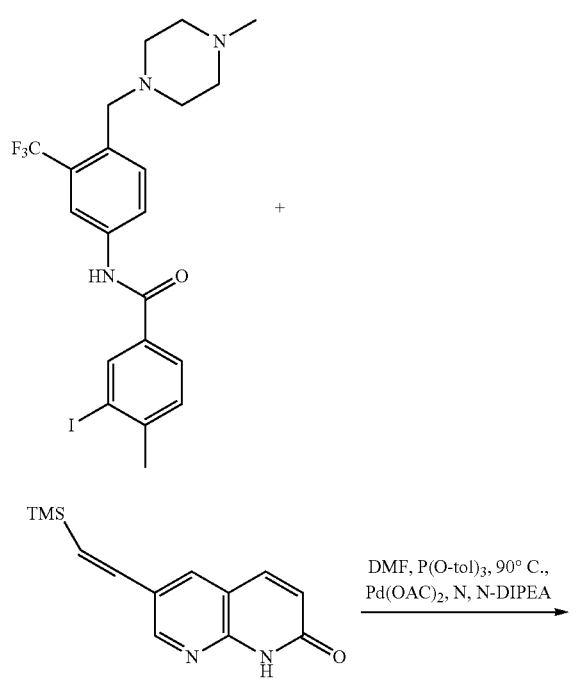

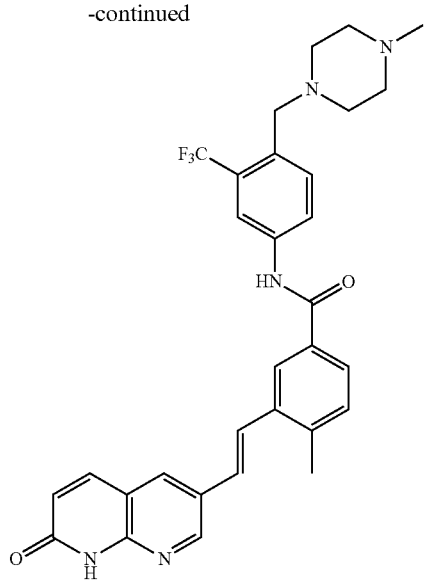

A mixture of 3-iodo-4-methyl-N-[4-[(4-methylpiperazin-1-yl)methyl]-3-(trifluoromethyl) phenyl]benzamide (1 equiv, prepared as per example SC5), 6-[2-trimethylsilylvinyl]-1H-1,8-naphthyridin-2-one (1 equiv,), Pd(OAC)$_2$ (0.1 equiv), P(O-tol)$_3$ (0.2 equiv), (i-Pr)$_2$EtN (4 equiv), in DMF was deoxygenated with Nitrogen gas for 30 minutes. Then heated to 90° C. for 7 h. Filtered through a pad of silica gel at room temperature, filtrate was concentrated, and the residue was purified by silica gel chromatography (eluted with 10% methanol/methylene chloride) to provide the title compound as a solid. The compound was subjected to hydrochloride salt formation using methanol and IPA-HCl.

$^1$HNMR (400 MHz, DMSOD$_6$) δ12.283 (s, 1H), 10.772-10.802 (s, 1H), 8.822 (s, 1H), 8.521 (s, 1H), 8.367 (s, 2H), 8.233 (s, 1H), 8.042 (s, 1H), 7.950-7.974 (d, 1H), 7.835-7.854 (d, 1H), 7.577-7.618 (d, 1H), 7.409-7.465 (d, 2H), 6.611-6.634 (d, 1H), 4.155 (bs, 2H), 3.075-3.550 (bs, 8H), 2.806 (s, 3H), 2.529 (s, 3H). ESI MS m/z −562.2 (M+H)$^+$.

Example-3

N-[4-Methyl-3-[2-(7-oxo-8H-1,8-naphthyridin-3-yl)ethynyl] phenyl]-4-[(4-methyl piperazin-1-yl)methyl]-3-(trifluoromethyl)benzamide (Development code: NRC19T)

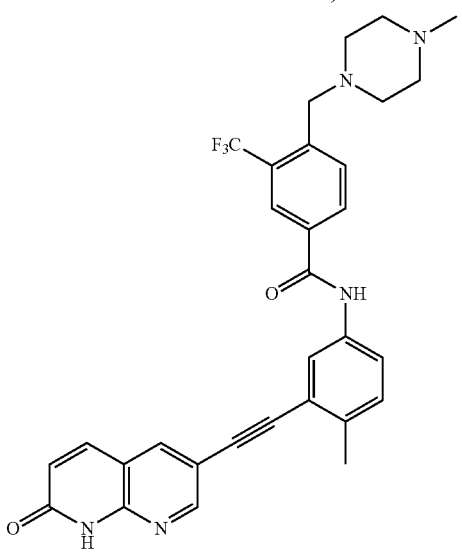

3.1 Methyl 4-methyl-3-(trifluoromethyl) benzoate

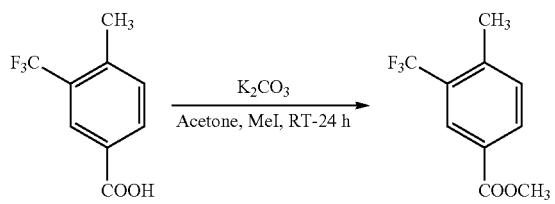

To a mixture of 4-methyl-3-(trifluoromethyl) benzoic acid (1 equiv), $K_2CO_3$ (1.5 equiv) in acetone (15 times) was added MeI (1.5 equiv) at room temperature. Stirring was continued for 24 h. Reaction was monitored by thin layer chromatography. The salts were filtered and resulting filtrate was concentrated, diluted with water, extracted with ethyl acetate. Concentration of organic layer afforded the pale yellow oil (95% yield). ESI MS m/z −219 (M+H'1)$^+$.

3.2 Methyl 4-(bromomethyl)-3-(trifluoromethyl) benzoate

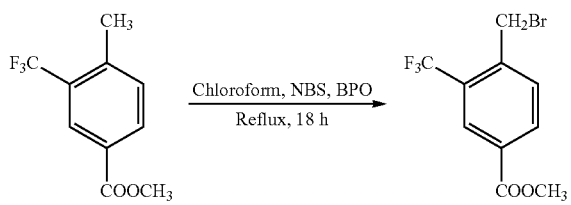

To a solution of methyl-4-methyl-3-(trifluoromethyl) benzoate (1 equiv) in chloroform was added N-bromosuccinimide (1.1 equiv) and benzoyl peroxide (0.01 equiv). The reaction mixture was heated at reflux overnight (18 h). It was then cooled to room temperature, washed with water, dried over $Na_2SO_4$ and concentrated. It was purified by silica gel chromatography (eluted with 1% ethyl acetate/hexane) to provide the title compound (65% yield). ESI MS m/z −297.

3.3 Methyl 4-[(4-methylpiperazin-1-yl)methyl]-3-(trifluoromethyl) benzoate

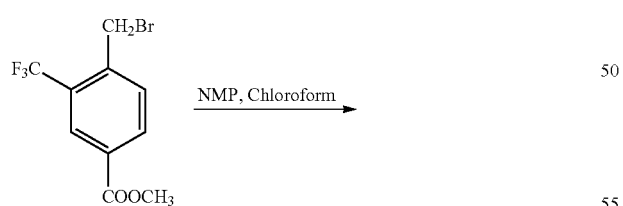

To a solution of methyl 4-(bromomethyl)-3-(trifluoromethyl) benzoate (1 equiv) in chloroform (6times) was added to N-methylpiperazine (3 equiv) at room temperature. The resulting solution was stirred for 3 hrs, the reaction mass was washed with water and concentrated with chloroform to get the product. (95% yield). ESI MS m/z −317 (M+H)$^+$.

3.4 4-[(4-Methylpiperazin-1-yl)methyl]-3-(trifluoromethyl) benzoic acid

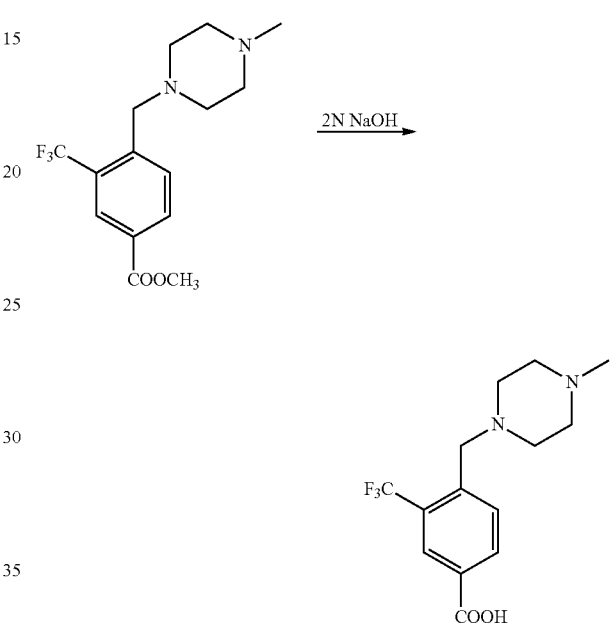

To a solution of methyl 4-[(4-methylpiperazin-1-yl)methyl]-3-(trifluoromethyl) benzoate (1 equiv) in ethanol (10times) was added 2N NaOH solution (2 equiv) at room temperature. The resulting solution was stirred for 3 h. The reaction mixture was concentrated and acidified with aqueous 2N HCl until a white solid formed. The compound was collected by filtration at 0-5° C. (85% yield). ESI MS m/z −303.3 (M+H)$^+$.

3.5 N-(3-iodo-4-methyl-phenyl)-4-[(4-methylpiperazin-1-yl) methyl]-3-(trifluoro methyl) benzamide

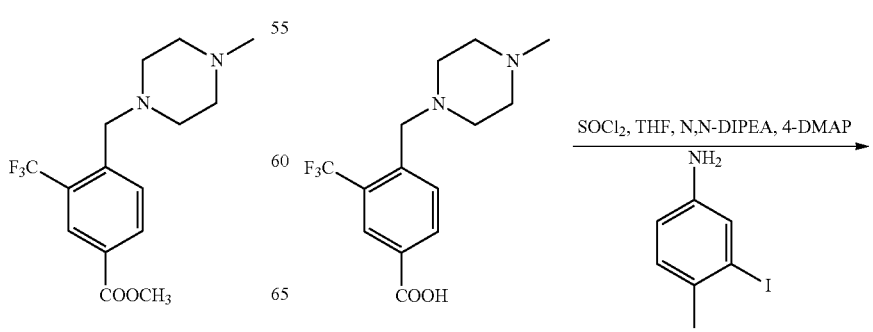

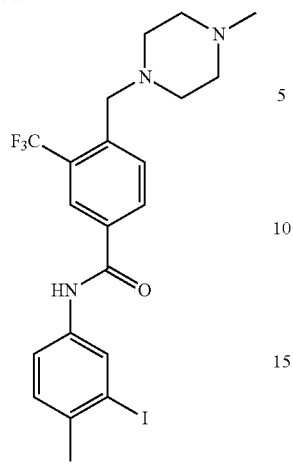

To a solution of 3-iodo-4-methyl aniline (0.7 equiv) in THF (10times) under nitrogen gas atmosphere was added 4-[(4-methylpiperazin-1-yl)methyl]-3-(trifluoromethyl)benzoyl chloride (1 equiv, prepared from the reaction of 4-[(4-methylpiperazin-1-yl)methyl]-3-(trifluoromethyl)benzoic acid and $SOCl_2$) in THF (4times) at room temperature for 30 minutes followed by drop wise addition of (i-Pr)$_2$EtN (4 equiv) and 4-DMAP (0.2 equiv). After stirring at ambient temperature for 120 min, the reaction mixture was quenched with water and extracted with ethyl acetate. The ethyl acetate layer was concentrated to provide the crude product. Acetone was added to this crude product and isolated as HCl salt by employing IPA-HCl (40% yield). ESI MS m/z −518 (M+H)$^+$.

3.6 N-[4-Methyl-3-[2-(7-oxo-8H-1,8-naphthyridin-3-yl) ethynyl] phenyl]-4-[(4-methyl piperazin-1-yl) methyl]-3-(trifluoromethyl)benzamide (Development code: NRC19T)

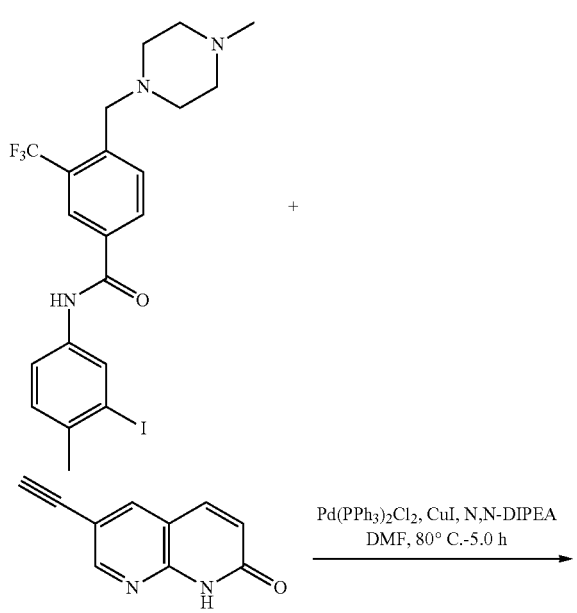

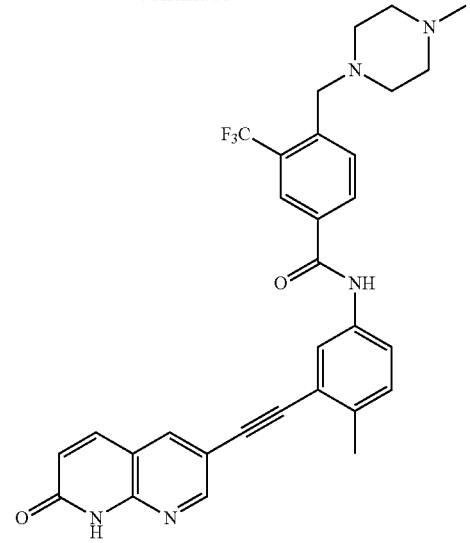

A mixture of N-(3-iodo-4-methyl-phenyl)-4-[(4-methyl-piperazin-1-yl)methyl]-3-(trifluoro methyl)benzamide (0.8 equiv, prepared as per 3.5), 6-ethynyl-1H-1,8-naphthyridin-2-one (1 equiv, prepared as per 1.5), Pd(PPh3)$_2$Cl$_2$ (0.1 equiv), CuI (0.15 equiv), (i-Pr)$_2$EtN (4 equiv), in DMF (20times) was deoxygenated with nitrogen gas for 30 minutes. Heated to 80° C. for 5 h and filtered through a pad of silica gel at room temperature. The filtrate was concentrated, diluted with water and stirred for 1 h. The compound was collected by filtration. Methanol was added to the above wet compound and the product was isolated as the HCl salt by employing IPA-HCl (40% yield).

$^1$HNMR (400 MHz, DMSOD$_6$) δ12.403 (s, 1H), 10.626 (s, 1H), 8.716-8.721 (s, 1H), 8.384-8.390 (s, 1H), 8.338-8.348 (d, 2H), 8.143 (s, 1H), 8.063-8.069 (s, 1H), 7.945-7.969 (d, 1H), 7.706-7.732 (d, 1H), 7.342-7.364 (d, 1H), 6.636-6.659 (d, 1H), 4.114 (bs, 2H), 2.894-3.502 (bs, 8H), 2.790 (s, 3H), 2.482 (s, 3H). ESI MS m/z −560.28 (M+H)$^+$.

Example-4

4-Methyl-N-[3-(4-methylimidazol-1-yl)-5-(trifluoromethyl) phenyl]-3-[2-(7-oxo-8H-1,8-naphthyridin-3-yl)ethynyl]benzamide Development code: NRC18T)

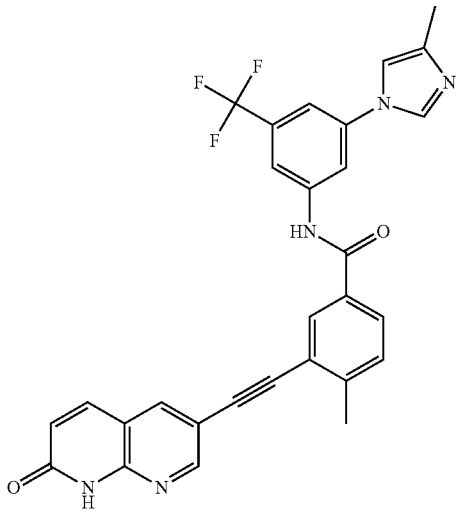 [SMILES: Cc1cn(-c2cc(NC(=O)c3ccc(C)c(C#Cc4cnc5[nH]c(=O)ccc5c4)c3)cc(C(F)(F)F)c2)cn1]

4.1 3-Iodo-4-methyl-N-[3-(4-methylimidazol-1-yl)-5-trifluoromethyl) phenyl] benzamide

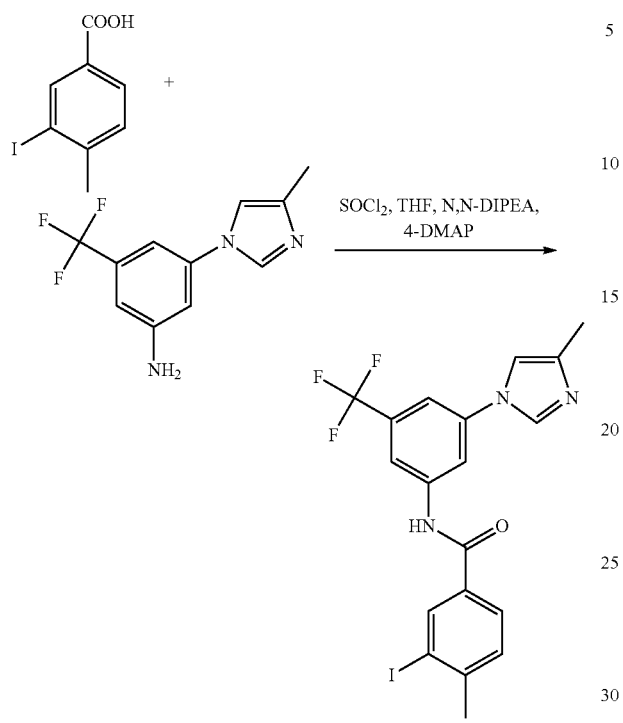

To a solution of 3-(4-methylimidazol-1-yl)-5-(trifluoromethyl)aniline (0.7 equiv, prepared according to literature known methods) in THF under nitrogen atmosphere was added 3-Iodo-4-methyl benzoyl chloride (1 equiv, prepared from the reaction of 3-iodo-4-methylbenzoic acid and $SOCl_2$) in THF at room temperature during 30 minutes followed by drop wise addition of (i-Pr)$_2$EtN (2 equiv) and 4-DMAP (0.2 equiv). After stirring at ambient temperature over 3 h, the reaction mixture was quenched with water. The resulting mixture was stirred at 0-5° C. for 60 min. Compound was collected by filtration. This compound was further purified by silica gel chromatography (eluted with 2% methanol/chloroform) to provide the title compound (85% yield). ESI MS m/z –486.2 (M+H)$^+$.

4.2 4-Methyl-N-[3-(4-methylimidazol-1-yl)-5-(trifluoromethyl) phenyl]-3-[2-(7-oxo-8H-1,8-naphthyridin-3-yl)ethynyl]benzamide (Development code: NRC18T)

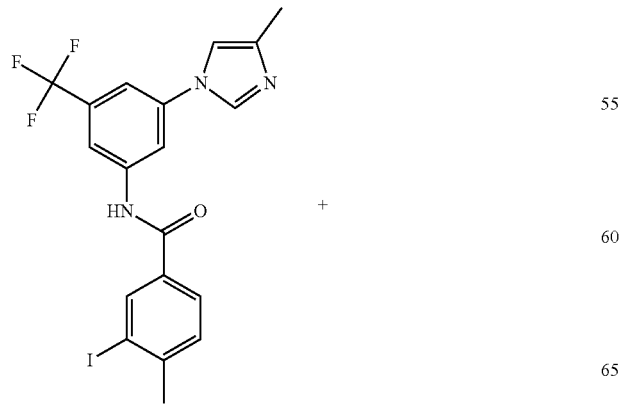

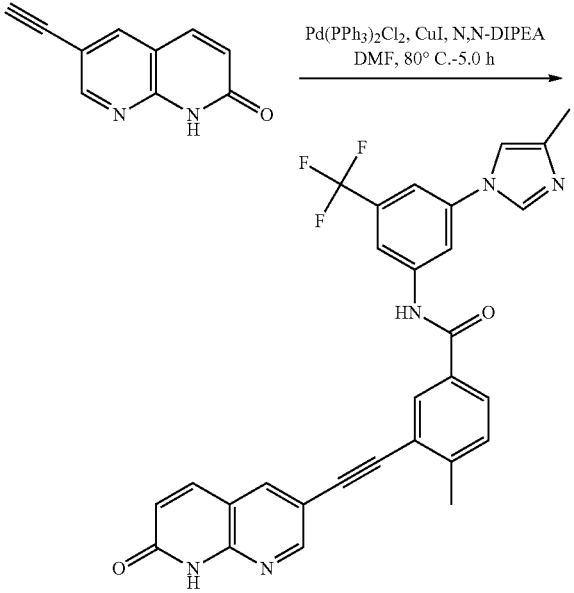

A mixture of 3-iodo-4-methyl-N-[3-(4-methylimidazol-1-yl)-5-(trifluoromethyl)phenyl] benzamide (0.8 equiv, prepared as per 4.1), 6-ethynyl-1H-1,8-naphthyridin-2-one (1 equiv, prepared as per 1.5), Pd(PPh3)$_2$Cl$_2$ (0.1 equiv), CuI (0.15 equiv), (i-Pr)$_2$EtN (4 equiv), in DMF (20 times) was deoxygenated with nitrogen gas for 30 minutes. Heated to 80° C. for 5 h, filtered through a pad of silica gel at room temperature. The filtrate was concentrated, diluted with water, stirred for 1 h and filtered. Acetone was added to above wet compound and the product was isolated as the HCl salt employing IPA-HCl (20% yield).

$^1$HNMR (400 MHz, DMSOD$_6$) δ12.440 (s, 1H), 11.034 (s, 1H), 9.668 (s, 1H), 8.736-8.741 (s, 1H), 8.634 (s, 1H), 8.392-8.397 (s, 1H), 8.320 (s, 1H), 8.252 (s, 1H), 7.950-8.051 (m, 4H), 7.557-7.577 (d, 1H), 6.647-6.671 (d, 1H), 2.591 (s, 3H), 2.377 (s, 3H). ESI MS m/z –528.27 (M+H)$^+$.

Example-5

4-Methyl-N-[3-[(4-methylpiperazin-1-yl) methyl]-5-(trifluoromethyl) phenyl]-3-[2-(7-oxo-8H-1,8-naphthyridin-3-yl)ethynyl]benzamide (Development code: NRC17T)

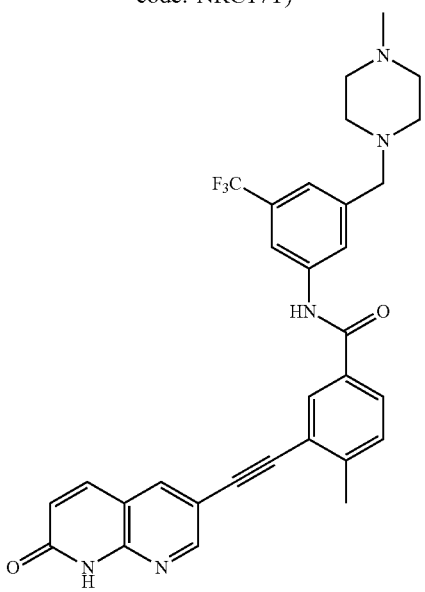

5.1 3-Iodo-4-methyl-N-[3-[(4-methylpiperazin-1-yl) methyl]-5-(trifluoromethyl) phenyl] benzamide

5.2 4-Methyl-N-[3-[(4-methylpiperazin-1-yl) methyl]-5-(trifluoromethyl) phenyl]-3-[2-(7-oxo-8H-1,8-naphthyridin-3-yl)ethynyl]benzamide (Development code: NRC17T)

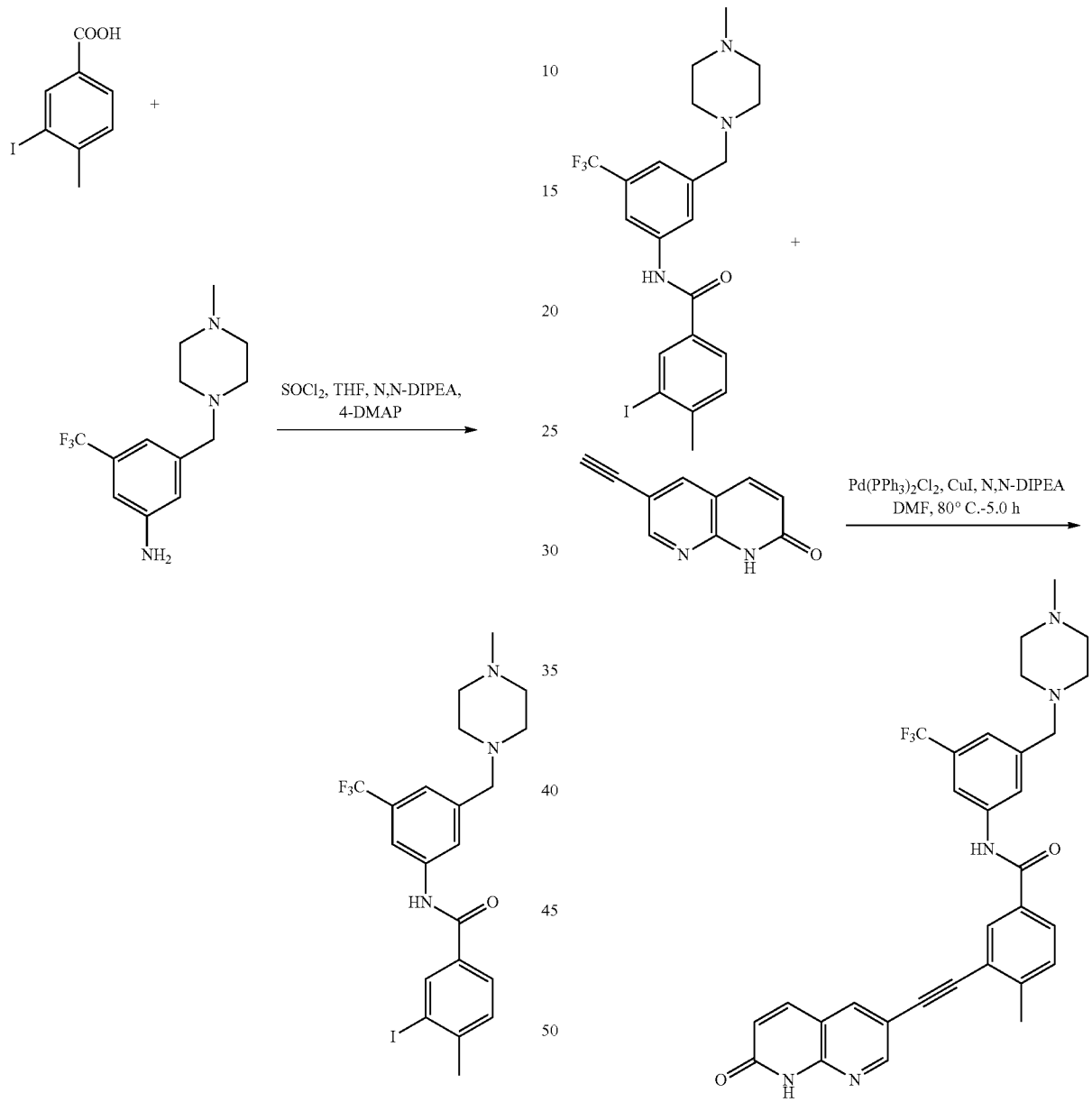

To a solution of 3-[(4-methylpiperazin-1-yl)methyl]-5-(trifluoromethyl)aniline (0.7 equiv, prepared according to literature methods) in THF under nitrogen atmosphere was added 3-Iodo-4-methyl benzoyl chloride (1 equiv, prepared from the reaction of 3-iodo-4-methylbenzoic acid and SOCl$_2$) in THF at room temperature during 30 minutes followed by drop wise addition of (i-Pr)$_2$EtN (2 equiv) and 4-DMAP (0.2 equiv). After stirring at ambient temperature over 3 h, the reaction mixture was quenched with water. The resulting mixture was extracted with ethyl acetate and formed product was isolated as HCl salt in acetone. ESI MS m/z –(M+1)$^+$.

A mixture of 3-iodo-4-methyl-N-[3-[(4-methylpiperazin-1-yl)methyl]-5-(trifluoromethyl) phenyl]benzamide (0.8 equiv, prepared as per 5.1), 6-ethynyl-1H-1,8-naphthyridin-2-one (1 equiv, prepared as per 1.5), Pd(PPh3)$_2$Cl$_2$ (0.1 equiv), CuI (0.15 equiv), (i-Pr)$_2$EtN (4 equiv), in DMF (20 times) was deoxygenated with Nitrogen gas for 30 minutes. Heated to 80° C. for 5 h, filtered through a pad of silica gel at room temperature. The filtrate was concentrated, diluted with water, stirred for 1 h and filtered. Methanol was added and the product was isolated as the HCl salt employing IPA-HCl (25% yield).

$^1$HNMR (400 MHz, DMSOD$_6$) δ12.432 (s, 1H), 10.796 (s, 1H), 8.741 (s, 1H), 8.399 (s, 1H), 8.322 (s, 1H), 8.222 (s,

2H), 7.964 (d, 2H), 7.814 (s, 1H), 7.542-(d, 1H), 6.647 (d, 1H), 4.363 (s, 2H), 3.394 (bs, 8H), 2.818 (s, 3H), 2.589 (s, 3H). ESI MS m/z −(M+1)⁺.

Example-6

N-[3,5-Bis (trifluoromethyl) phenyl]-4-methyl-3-[2-(7-oxo-8H-1,8-naphthyridin-3-yl)ethynyl]benzamide benzamide (Development code: NRC16T)

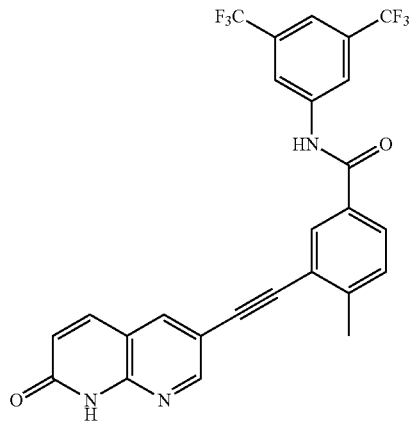 [SMILES: Cc1ccc(C(=O)Nc2cc(C(F)(F)F)cc(C(F)(F)F)c2)cc1C#Cc1cnc2[nH]c(=O)ccc2c1]

6.1 N-[3,5-Bis (trifluoromethyl) phenyl]-3-iodo-4-methyl-benzamide

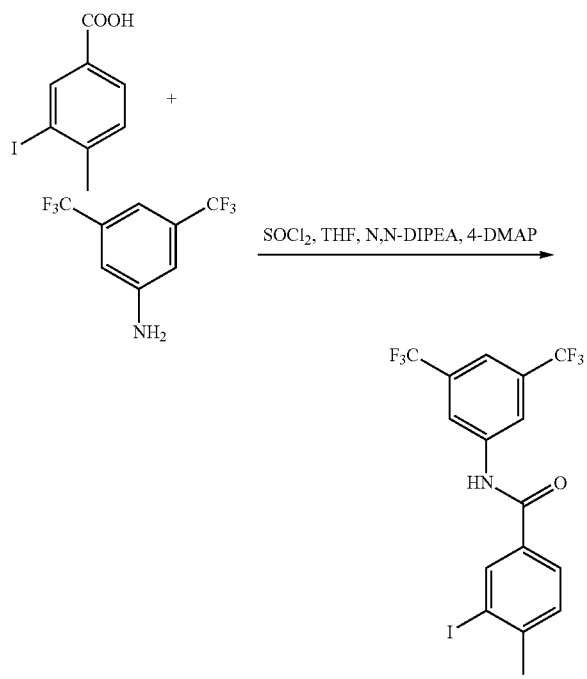

To a solution of 3,5-bis trifluoro methyl aniline (0.7 equiv) in THF (6times) under Nitrogen gas atmosphere was added 3-Iodo-4-methyl benzoyl chloride (1 equiv, prepared from the reaction of 3-iodo-4-methylbenzoic acid and SOCl₂) in THF at room temperature during 30 minutes followed by drop wise addition of (i-Pr)₂EtN (2 equiv) and 4-DMAP (0.2 equiv). After stirring at ambient temperature over 3 h, the reaction mixture was quenched with water. The resulting mixture was extracted with ethyl acetate and concentrated. Acetone was added to the resulting residue and formed HCl salt using IPA-HCl (85% yield). ESI MS m/z −474 (M+H)⁺.

6.2 N-[3,5-Bis (trifluoromethyl) phenyl]-4-methyl-3-[2-(7-oxo-8H-1, 8-naphthyridin-3-yl) ethynyl] benzamide (Development code: NRC16T)

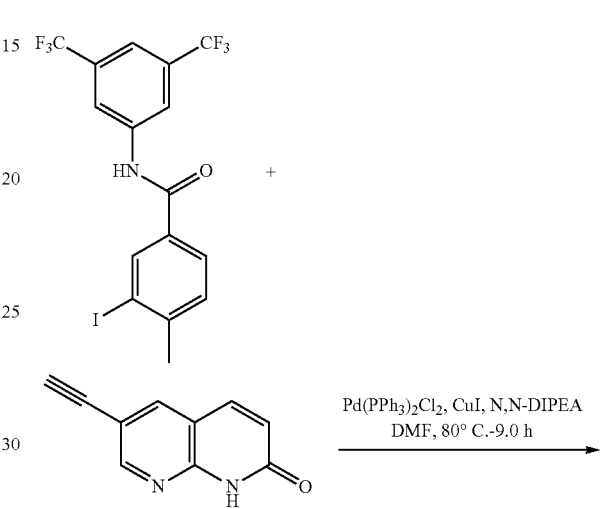

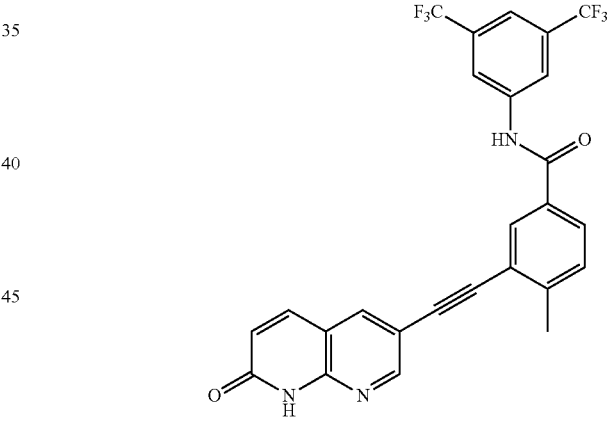

A mixture of N-[3,5-bis(trifluoromethyl)phenyl]-3-iodo-4-methylbenzamide (0.8 equiv, prepared as per 6.1), 6-ethynyl-1H-1,8-naphthyridin-2-one (1 equiv, prepared as per 1.5), Pd(PPh3)₂Cl₂ (0.1 equiv), CuI (0.15 equiv), (i-Pr)₂EtN (4 equiv), in DMF was deoxygenated with nitrogen gas for 30 minutes. Heated to 80° C. for 9 h, filtered through a pad of silica gel at room temperature. The filtrate was concentrated, diluted with water, stirred for 1 h and filtered. Methanol was added and the compound was filtered as HCl salt by treatment with IPA-HCl (60% yield).

¹HNMR (400 MHz, DMSOD₆) δ12.429 (s, 1H), 10.874 (s, 1H), 8.746 (s, 1H), 8.545 (s, 2H), 8.402 (s, 1H), 8.223 (s, 1H), 7.956-7.979 (d, 2H), 7.839 (s, 1H), 7.563-7.582 (d, 1H), 6.646-6.668 (d, 1H), 2.594 (s, 3H). ESI MS m/z −516.13 (M+H)⁺.

Example-7

N-[4-Methyl-3-[2-(7-oxo-8H-1,8-naphthyridin-3-yl)ethynyl] phenyl]-3,5-bis (trifluoro methyl)benzamide benzamide (Development code: NRC15T)

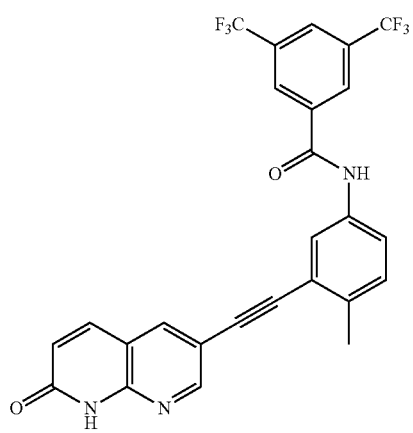 [SMILES: Cc1ccc(NC(=O)c2cc(C(F)(F)F)cc(C(F)(F)F)c2)cc1C#Cc1cnc2[nH]c(=O)ccc2c1]

7.1 N-(3-iodo-4-methyl-phenyl)-3,5-bis (trifluoromethyl)benzamide

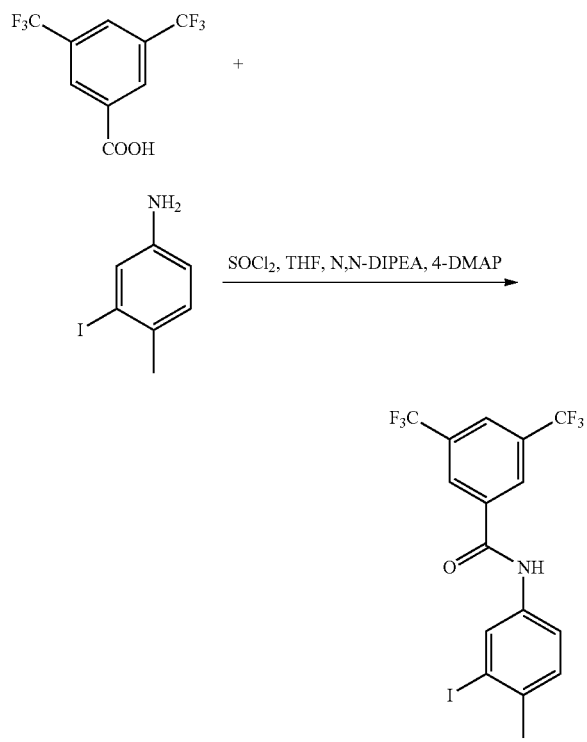

To a solution of 3-Iodo-4-methyl aniline (0.7 equiv) in THF (6times) under nitrogen atmosphere was added 3,5-bis trifluoromethylbenzoyl chloride (1 equiv, prepared from the reaction of 3,5-bis trifluoromethylbenzoic acid and $SOCl_2$) in THF at room temperature for 30 minutes followed by drop wise addition of (i-Pr)$_2$EtN (4 equiv) and 4-DMAP (0.2 equiv). After stirring at ambient temperature for 3 h, the reaction mixture was quenched with water. The resulting mixture was extracted with ethyl acetate, concentrated and the compound was collected by adding hexane and filtration (44% yield).

7.2 N-[4-Methyl-3-[2-(7-oxo-8H-1,8-naphthyridin-3-yl)ethynyl]phenyl]-3,5-Bis (trifluoro methyl)benzamide (Development code: NRC15T)

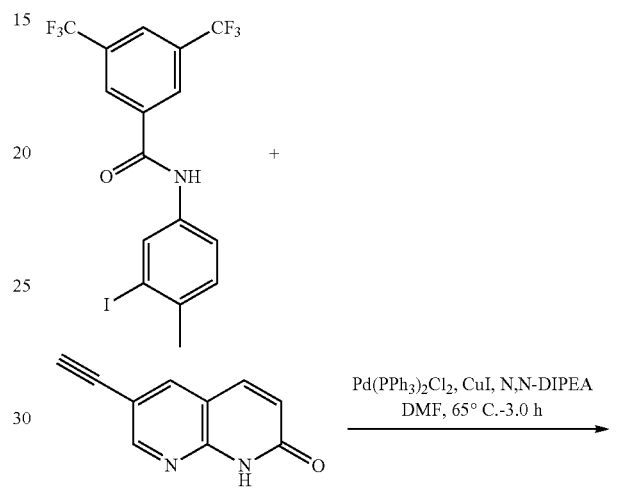

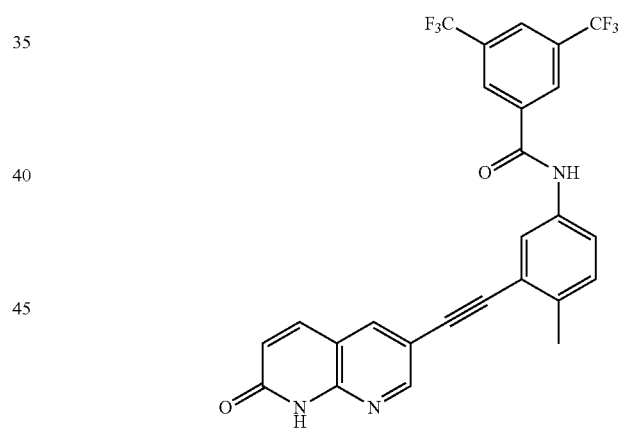

A mixture of N-(3-iodo-4-methyl-phenyl)-3,5-bis(trifluoromethyl)benzamide (0.8 equiv, prepared as per 7.1), 6-ethynyl-1H-1,8-naphthyridin-2-one (1 equiv, prepared as per example 1.5), Pd(PPh3)$_2$Cl$_2$ (0.1 equiv), CuI (0.15 equiv), (i-Pr)$_2$EtN (4 equiv), in DMF was deoxygenated with nitrogen gas for 30 minutes. Heated to 65° C. for 3 h and filtered through a pad of silica gel at room temperature. The filtrate was diluted with water and extracted with ethyl acetate. Ethyl acetate layer was concentrated and formed HCl salt in acetone solvent.

$^1$HNMR (400 MHz, DMSO D$_6$) δ12.403 (s, 1H), 10.743 (s, 1H), 8.716 (s, 1H), 8.636 (s, 2H), 8.382 (s, 2H), 8.039 (s, 1H), 7.942 (d, 1H), 7.701 (d, 1H), 7.365 (d, 1H), 6.635 (d, 1H), 2.490 (s, 3H). ESI MS m/z –(M+H)$^+$.

Example-8

4-Methyl-3-[2-(7-oxo-8H-1,8-naphthyridin-3-yl) ethynyl]-N-[3-(trifluoromethyl) phenyl] benzamide benzamide (Development code: NRC14T)

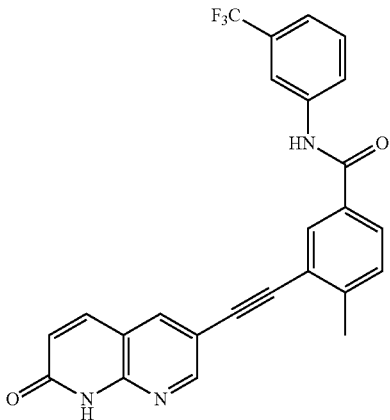 [SMILES: Cc1ccc(C(=O)Nc2cccc(C(F)(F)F)c2)cc1C#Cc1cnc2[nH]c(=O)ccc2c1]

8.1 3-Iodo-4-methyl-N-[3-(trifluoromethyl) phenyl] benzamide

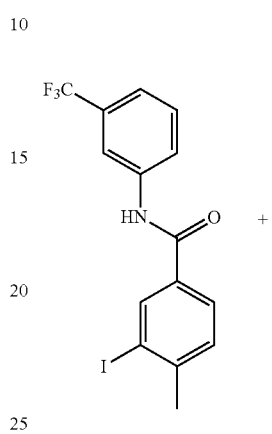

To a solution of 3-trifluoromethyl aniline (0.7 equiv) in THF under nitrogen atmosphere was added 3-Iodo-4-methyl benzoyl chloride (1 equiv, prepared from the reaction of 3-iodo-4-methylbenzoic acid and SOCl₂) in THF at room temperature during 30 minutes followed by drop wise addition of (i-Pr)₂EtN (2 equiv) and 4-DMAP (0.2 equiv). After stirring to ambient temperature over 3 h, the reaction mixture was quenched in to water. The resulting mixture was extracted with ethyl acetate and concentrated. The compound was collected by filtration using hexane solvent (49.2% yield). ESI MS m/z −(M+1)⁺.

8.2 4-Methyl-3-[2-(7-oxo-8H-1,8-naphthyridin-3-yl) ethynyl]-N-[3-(trifluoromethyl) phenyl] benzamide (Development code: NRC14T)

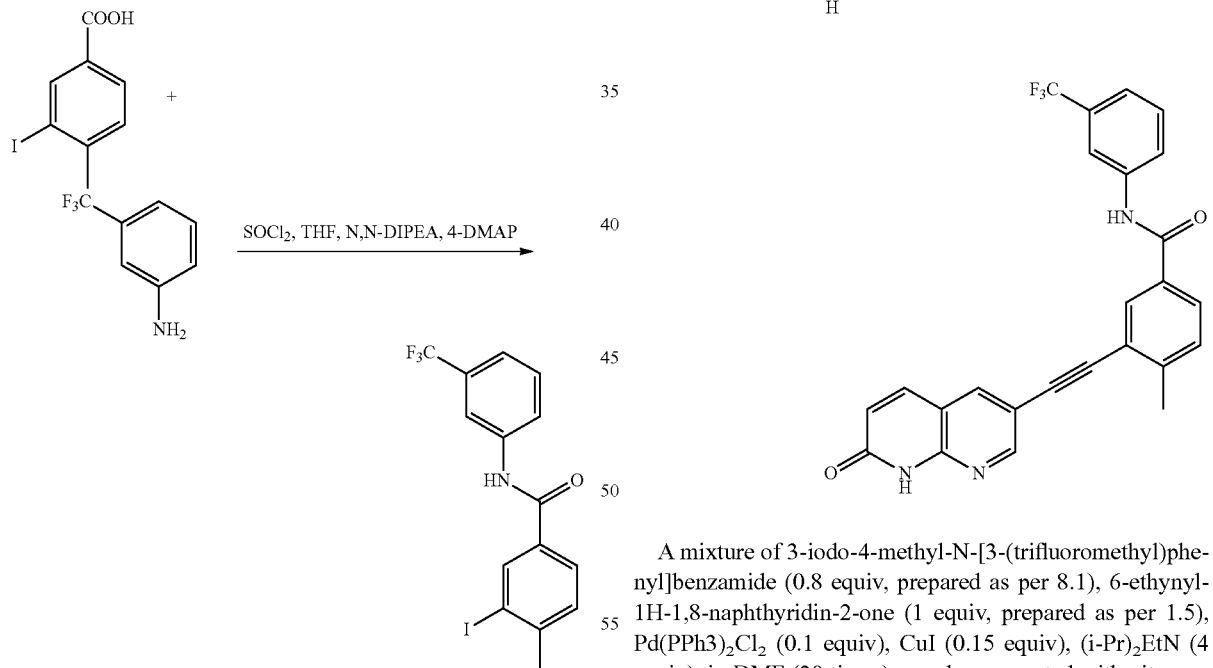

A mixture of 3-iodo-4-methyl-N-[3-(trifluoromethyl)phenyl]benzamide (0.8 equiv, prepared as per 8.1), 6-ethynyl-1H-1,8-naphthyridin-2-one (1 equiv, prepared as per 1.5), Pd(PPh3)₂Cl₂ (0.1 equiv), CuI (0.15 equiv), (i-Pr)₂EtN (4 equiv), in DMF (20 times) was deoxygenated with nitrogen gas for 30 minutes. Heated to 65° C. for 3 h, filtered through a pad of silica gel at room temperature and filtrate was diluted with water. The compound was collected by filtration and HCl salt formation.

¹HNMR (400 MHz, DMSOD₆) δ12.426 (s, 1H), 10.595 (s, 1H), 8.742 (s, 1H), 8.395 (s, 1H), 8.260 (s, 1H), 8.192 (s, 1H), 8.079 (d, 1H), 7.935 (d, 2H), 7.596 (t, 1H), 7.533 (d, 1H), 7.459 (d, 1H), 6.644 (d, 1H), 2.587 (s, 3H). ESI MS m/z −(M+H)⁺.

Example-9

N-[4-Methyl-3-[2-(7-oxo-8H-1,8-naphthyridin-3-yl)ethynyl]phenyl]-3-(trifluoromethyl) benzamide benzamide (Development code: NRC13T)

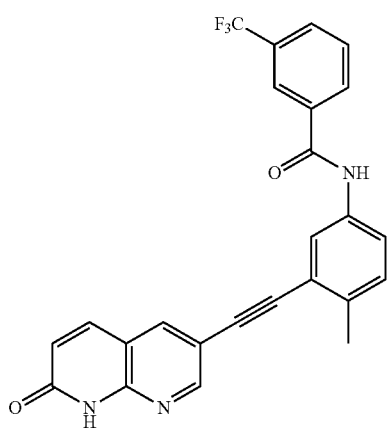 [SMILES: Cc1ccc(NC(=O)c2cccc(C(F)(F)F)c2)cc1C#Cc1cnc2[nH]c(=O)ccc2c1]

9.1 N-(3-iodo-4-methyl-phenyl)-3-(trifluoromethyl) benzamide

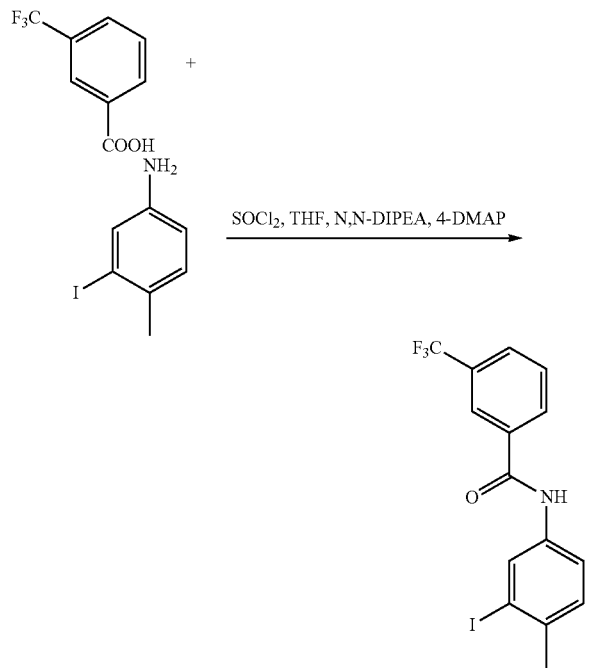

To a solution of 3-iodo-4-methyl aniline (0.7 equiv) in THF under nitrogen atmosphere was added 3-trifluoro methyl benzoyl chloride (1 equiv, prepared from the reaction of 3-trifluoromethyl benzoic acid and SOCl$_2$) in THF at room temperature during 30 minutes followed by drop wise addition of (i-Pr)$_2$EtN (4 equiv) and 4-DMAP (0.2 equiv). After stirring at ambient temperature for 3 h, the reaction mixture was quenched with water. The resulting mixture was extracted with ethyl acetate, concentrated and the compound was isolated by adding n-hexane.

9.2 N-[4-Methyl-3-[2-(7-oxo-8H-1,8-naphthyridin-3-yl)ethynyl]phenyl]-3-(trifluoro methyl) benzamide (Development code: NRC13T)

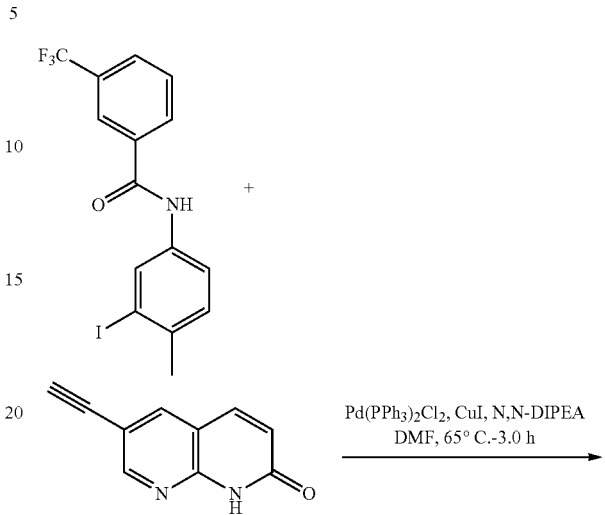

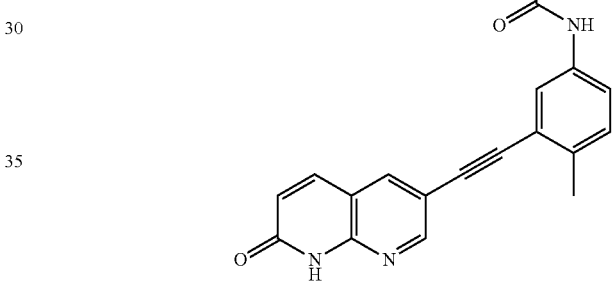

A mixture of N-(3-iodo-4-methyl-phenyl)-3-(trifluoromethyl)benzamide (0.8 equiv, prepared as per 9.1), 6-ethynyl-1H-1,8-naphthyridin-2-one (1 equiv, prepared as per 1.5), Pd(PPh3)$_2$Cl$_2$ (0.1 equiv), CuI (0.15 equiv), (i-Pr)$_2$EtN (4 equiv), in DMF was deoxygenated with nitrogen gas for 30 minutes. Heated to 65° C. for 3 h, filtered through a pad of silica gel at room temperature and the filtrate was diluted with water. The resulting mixture was stirred for 1 h and the compound was collected by filtration and HCl salt using IPA-HCl.

$^1$HNMR (400 MHz, DMSOD$_6$) δ12.400 (s, 1H), 10.523 (s, 1H), 8.718 (s, 1H), 8.381 (s, 1H), 8.317 (s, 1H), 8.272 (d, 1H), 8.055 (s, 1H), 7.940 (d, 2H), 7.786 (t, 1H), 7.704 (d, 1H), 7.343 (d, 1H), 6.635 (d, 1H), 2.484 (s, 3H). ESI MS m/z −(M+H)$^+$.

Example-10

In vitro Efficacy Evaluation:

All the experimental compounds were evaluated for in vitro efficacy employing standard cell lines used for the screening of anti-cancer compounds.

Ponatinib was used as reference drug candidate for a comparative efficacy and safety evaluation. A laboratory sample of the drug substance Ponatinib was synthesized in house employing the procedure disclosed in U.S. Pat. No. 8,114,874.

In Vitro Studies of NRC-21T on BCR-Abl Positive Cell Line K562 and Mutant Cell Lines Baf3/T315i, M351T, E255K and WT.

Figure 3:
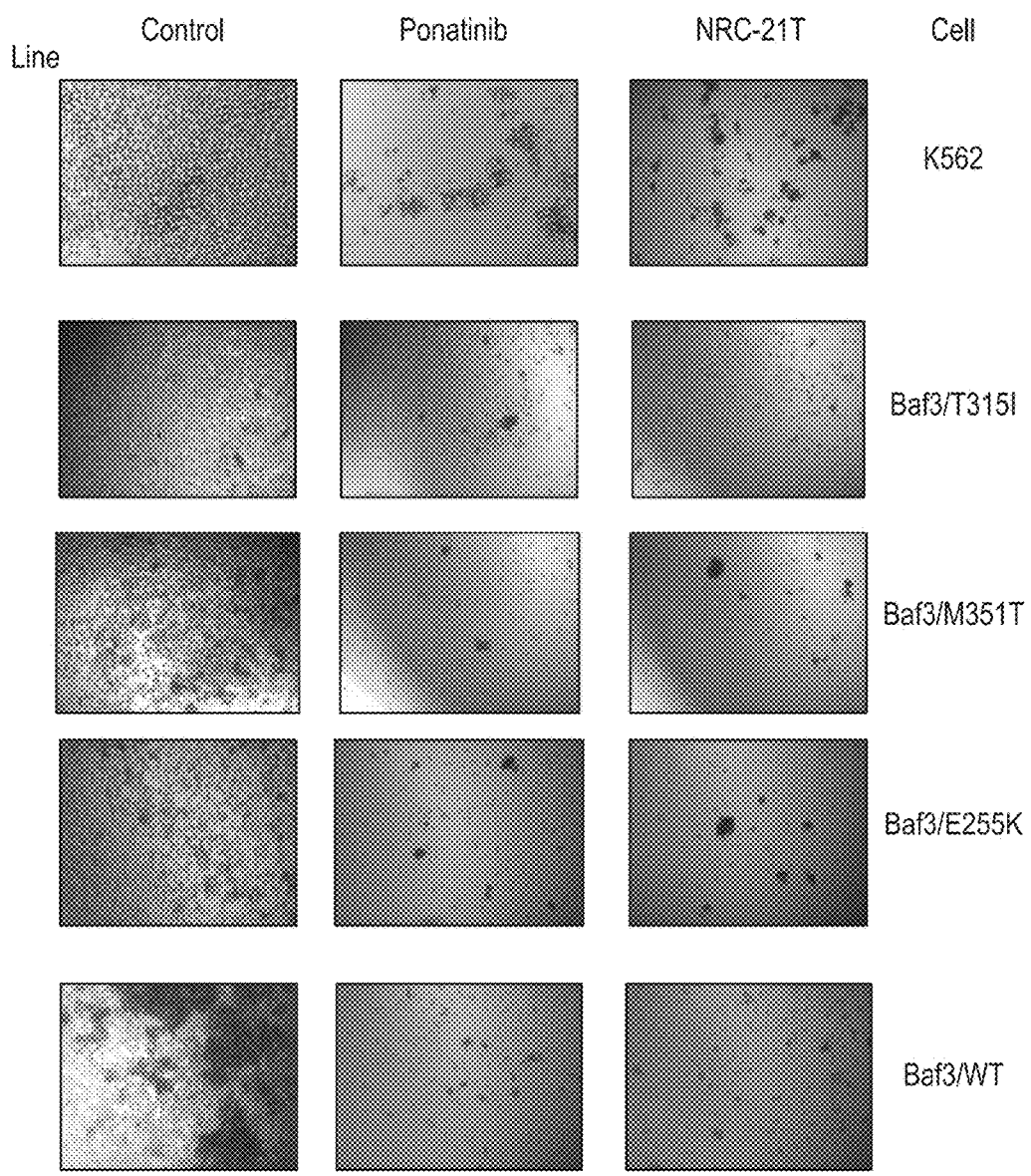
FIG. 3 shows Anti-proliferative activity of NRC-21T on various Leukemial cell lines

The experimental compounds and the standard reference drug (Ponatinib) were dissolved in cell culture medium and DMSO at a concentration of 10 mM for in vitro studies. The stock solution was further diluted with the same cell culture medium and used in concentrations of 0.1 nm to 10 μm. Cell proliferation by MTT assay was done as follows. 1000 to 10,000 cells were seeded per well in 96-well plate and different concentrations of Pon-21T ranging from 10 μm to 0.1 nM were added in triplicates. After incubating the cells with NRC-21T for the required time period 24-72 hrs, 15 μl of 5 mg/ml MTT was added and incubated for additional 4 hours at 37° C. and 5% $CO_2$. After 4 hrs, formazan crystals were dissolved in solubilizing buffer overnight at 37° C. Absorbance was measured on Elisa reader at dual wavelength of 570-630-nm. By MTT assay the $IC_{50}$ values of the NRC21T were computed. $IC_{50}$ values obtained by MTT assay were tabulated in Table-1A & Table-1B and cells of control, Ponatinib and NRC21T was photo graphed under inverted microscope and presented. (FIG. 3)

TABLE 1A $IC_{50}$ values obtained from MTT assay

| Name of the Cell line | Name of the Molecule/IC50 values (nM) | |
|---|---|---|
| | PONATINIB | NRC21T (Example-1) |
| Baf3/T315I | 8 | 14 |
| Baf3/M351T | 2 | 2 |
| Baf3/E255K | 15 | 16 |
| Baf3/WT | 1 | 11 |
| K562 | 4 | 7 |

TABLE 1B

IC50 values obtained from MTT assay

| | | IC/50 values (nM) | |
|---|---|---|---|
| S. No. | Name of the molecule | K562 | T315I |
| 1. | Ponatinib | 4 | 11 |
| 2. | NRC-20T (Example-2) | 33 | 155 |
| 3. | NRC-19T (Example-3) | 7 | 334 |
| 4. | NRC-18T (Example-4) | Not done | 228 |
| 5. | NRC-17T (Example-5) | 21 | 712 |
| 6. | NRC-16T (Example-6) | Not done | >10000 |
| 7. | NRC-15T (Example-7) | 20 | 7691 |
| 8. | NRC-14T (Example-8) | 8 | 1039 |
| 9. | NRC-13T (Example-9) | 9 | 1508 |

Example-11

Figure 4:
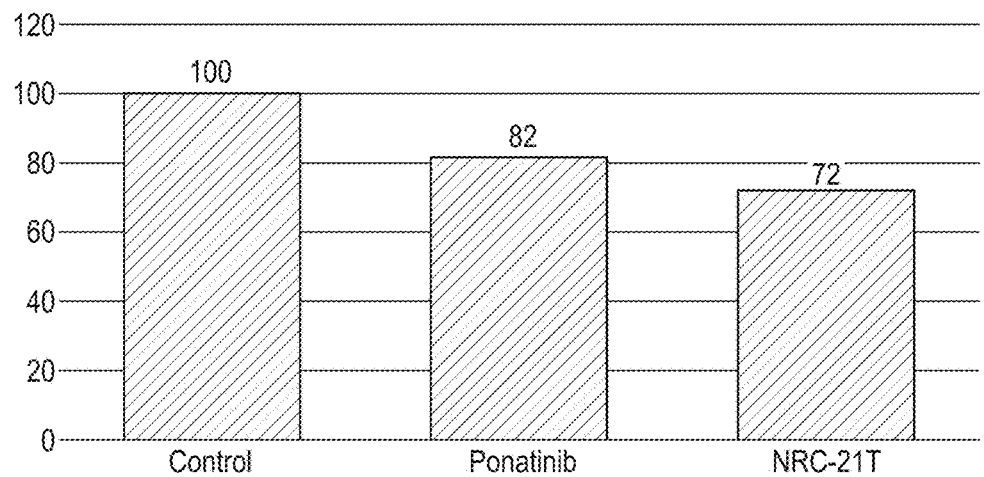
FIG. 4 shows Anti-Invasive property of NRC-21T on Baf3/T315I Cell line

Matrigel Invasion Assay:

The in-vitro invasiveness of BaF3/T315i mutant Leukemia cancer cells in the presence of specified concentration of NRC21T were assessed. T315i cells ($3\times10^5$) were suspended in 300 μl of serum-free medium and placed in the upper compartment of transwell chambers pre-coated with the matrigel (Millipore, Catalog No. ECM550, USA). The lower compartment of the chamber was filled with 500 μl serum-medium (10% FBS) and the cells were allowed to migrate for 72 hrs. After incubation, the cells were fixed and stained with the dye provided along with the kit and quantified using Elisa plate reader at 560 nm. In Vitro matrigel assay of T315i cells in the presence of specified concentration of NRC-21T were represented in Table 2 and FIG. 4.

TABLE 2

Anti-Invasive property of NRC-21T on T315i cell line

| Cell line | Test product | Percentage of Anti-invasion property |
|---|---|---|
| BaF3/T315I | Ponatinib | 12% |
| | NRC-21T | 28% |

Example-12

Determination of MTD of NRC21T [the MTD Study was Carried Out as Per OECD Guidelines 420]

The study was carried out using 5 (2 Male+3 Female) Swiss Albino Mice weighing 18-30 grams. All the animals were fasted for 3 hours prior to the oral administration of the drug. The sample was administered immediately to all the animals according to their body weight. After administration of the experimental drug all the animals were observed for ½ hr, 1 hr, 2 hr, 4 hours and mortality was observed for 14 days. At the end of 14 days, all the surviving animals were autopsied and stomach was cut opened and observed for absorption of the drug through the GIT.

NRC21T: MTD>2000 mg·kg, p.o (Single dose 14 days observation)

Ponatinib: MTD=50 mg/kg, p.o (Single dose 14 days observation)

CONCLUSION

Since the MTD of NRC21T is more than 2000 mg/kg, p.o according to ICH guidelines it is inferred that NRC21T is a safer experimental drug than Ponatinib. Also NRC21T has comparable $IC_{50}$ values with respect to Ponatinib. Thus, the experimental drug of this invention, NRC21T is established as superior candidate in terms of safety and efficacy.

Example-12

Establishment of Antagonism of NRC21T in T315I Induced Tumour in Nude Mice: [Clackson Etal. 2009, Cancer Cells November 6; 16(5): 401-412]

The study was carried out with 18 Nude Mice (9 Male+9 Female). Weighing of Nude mice was taken initially before inoculation of cell line and made into groups as follows:

Group-I: Positive control (3 Male+3 Female)
Group-II: NRC21T (3 Male+3 Female)
Group-III: Ponatinib (3 Male+3 Female)

The cell line was inoculated into Nude Mice subcutaneously to the right hind limb flank at a strength of $1\times10^6$ cells/0.2 ml. Animals were observed daily for the appearance of tumour. The tumour volume was measured using the formula ½ $lxw^2$ (l=length of tumour & w=width of tumour). When the mean tumour volume was recorded above 400 $mm^3$, the treatment with the above drugs was started. The above drugs were administered orally daily for 30 days. Weights of Nude Mice were taken daily before dosing and tumour measurements were done on alternative days using digital Vernier caliper. Surviving animals were sacrificed after the dosing was complete for 30 days and the organs (tumour with skin and spleen) were collected.

Figure 5:
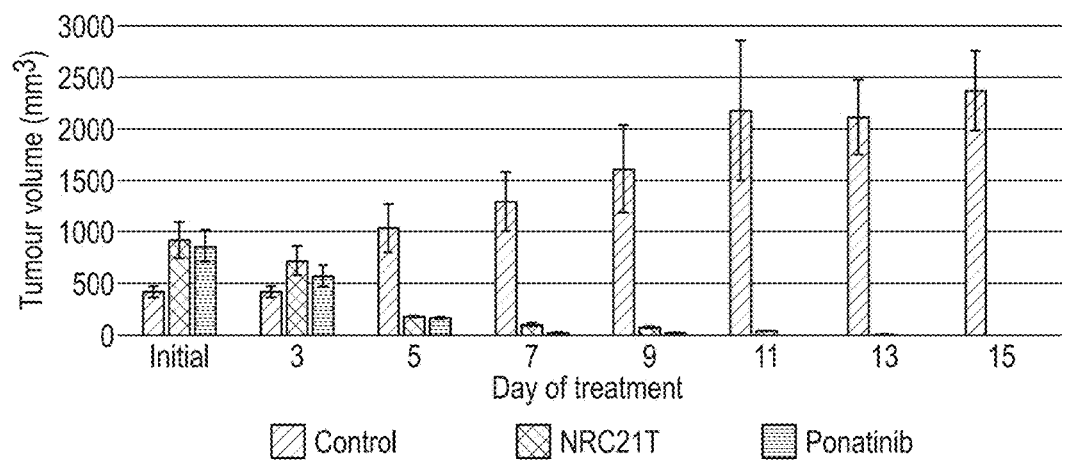
FIG. 5 shows Establishment of Antagonism of NRC21T in T315I induced tumour in Nude Mice
Figure 5B:
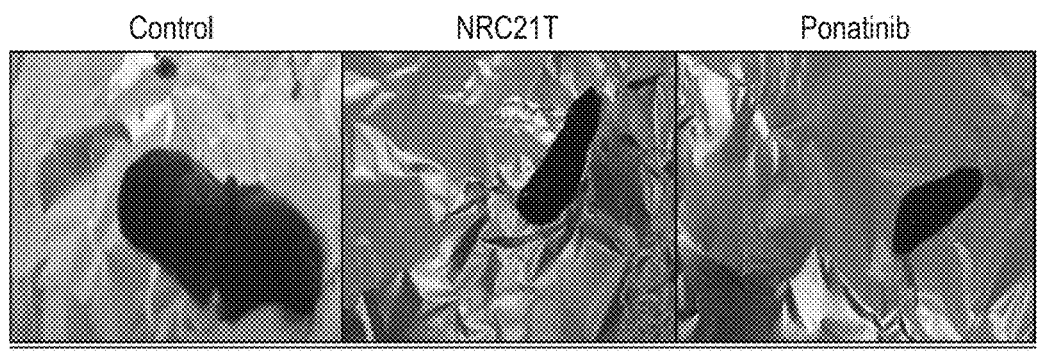
FIG. 5B shows Establishment of Antagonism of NRC21T in T315I induced tumour in nude mice, pictures of spleen

The study was depicted in FIG. 5, FIG. 5A and FIG. 5B.

| S. No | Group | No. of animals | Initial tumour volume (Mean ± SEM) (mm³) | Tumour volume after treatment (Mean ± SEM)(mm³) | | | | | | |
|---|---|---|---|---|---|---|---|---|---|---|
| | | | | 3rd Day | 5th Day | 7th Day | 9th Day | 11th Day | 13th Day | 15th Day |
| I | Control (2% Gum acacia + 2% SLS) | 6 | 418.91 ± 51.96 | 418.91 ± 51.96 | 1033.8 ± 234.44 | 1289.98 ± 291.38 | 1609.66 ± 427.58 | 2174.92 ± 678.99 | 2111.92 ± 360.31 | 2367.41 ± 384.49 |
| II | NRC21T (200 mg/kg, p.o) | 6 | 921.35 ± 176.32 | 721.18 ± 141.41 | 183.97 ± 8.66 | 106.59 ± 11.90 | 83.21 ± 8.83 | 48.88 ± 4.36 | 10.61 ± 2.3 | Tumour was completely absent |
| III | Ponatinib (50 mg/kg, p.o) | 6 | 864.59 ± 155.55 | 574.59 ± 103.13 | 168.23 ± 13.92 | 25.59 ± 8.27 | 22.59 ± 4.45 | All the mice were dead | 0 | 0 |

Example-13

Establishment of Survival Time of NRC21T in SCID Mice [Clackson Etal. 2009, Cancer Cells November 6; 16(5): 401-412]

The study was carried out using 30 SCID Mice (15 Male+15 Female). All the SCID Mice were injected with T315I cell Line intravenously to the tail vein at a strength of $1 \times 10^6$ cells/0.1 ml. grouping as follows:

Group-I: Positive Control (5 Male+5 Female) (Vehicle treated)

Group-II: NRC21T (5 Male+5 Female) (200 mg/kg, p.o)

Group-III: Ponatinib (5 Male+5 Female) (10 mg/kg, p.o)

Figure 6A:
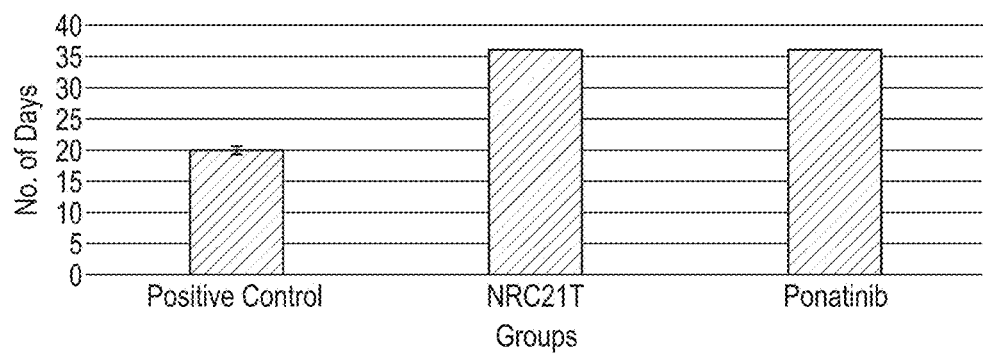
FIG. 6A shows Survival time study of NRC21T
Figure 6B:
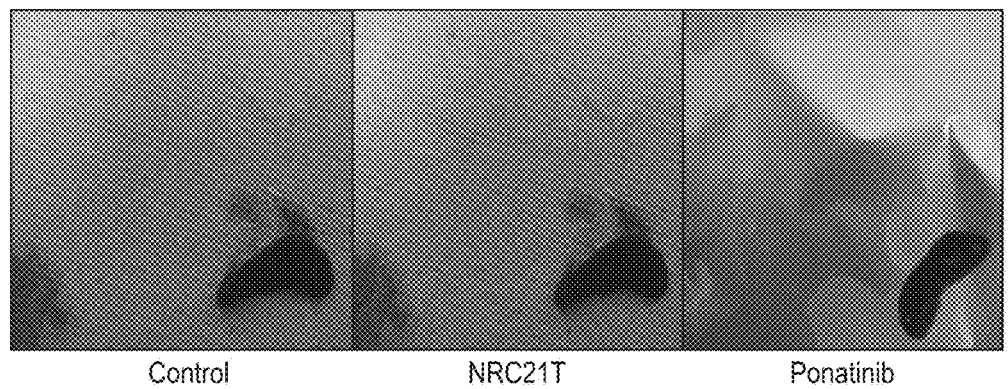
FIG. 6B shows Pictures of spleen under survival time study

After 72 hours of injection administration of drugs to the respective groups were started. All the animals in the groups were administered with the respective drugs for 30 days. In case of mortality during the study spleen and liver were collected and sent for histopathology. Animals in the moribund state were sacrificed and spleen and liver were collected and sent for histology. The study results depicted in FIG. 6A and FIG. 6B.

Results:

| | | Survival Time |
|---|---|---|
| S. No. | Group | Mean Survival Time (Mean ± SEM) (days) |
| 1 | Positive Control | 20 ± 0.68 |
| 2 | NRC21T | 36 ± 0 |
| 3 | Ponatinib | 36 ± 0 |

We claim:

1. A compound of formula I or an N-oxide or pharmaceutically acceptable salt thereof:

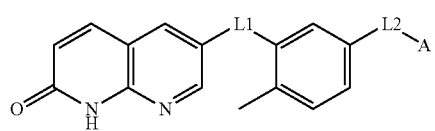

Formula (I)

wherein:

L1 is a linker selected from a carbon-carbon triple bond or a carbon-carbon double bond;

L2 is a linker selected from —NHC(O)—, —C(O)NH—; and

A is selected from the group consisting of:

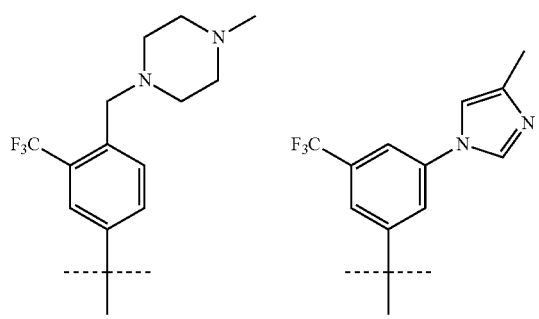

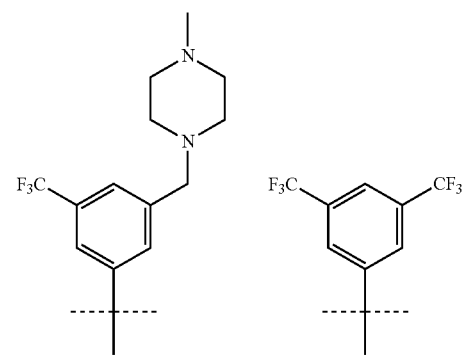

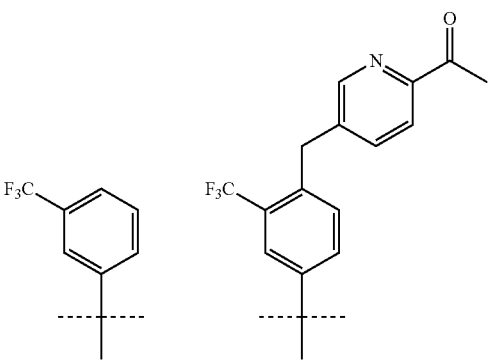

-continued

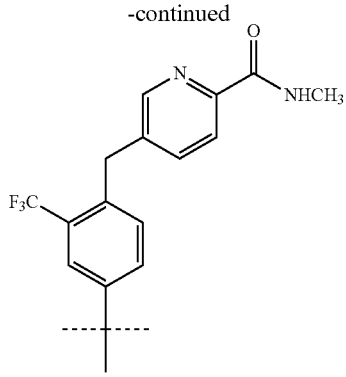

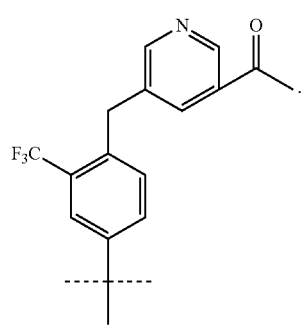

2. The compound according to claim 1 or an N-oxide or pharmaceutically acceptable salt thereof, which compound is selected from the group consisting of:
   a. 4-methyl-N-[4-[(4-methylpiperazin-1-yl)methyl]-3-(trifluoromethyl)phenyl]-3-[2-(7-oxo-8H-1,8-naphthyridin-3-yl)ethynyl]benzamide;
   b. 4-methyl-N-[4-[(4-methylpiperazin-1-yl)methyl]-3-(trifluoromethyl)phenyl]-3-[(E)-2-(7-oxo-8H-1,8-naphthyridin-3-yl)vinyl]benzamide;
   c. N-[4-methyl-3-[2-(7-oxo-8H-1,8-naphthyridin-3-yl)ethynyl]phenyl]-4-[(4-methylpiperazin-1-yl)methyl]-3-(trifluoromethyl)benzamide;
   d. 4-methyl-N-[3-(4-methylimidazol-1-yl)-5-(trifluoromethyl)phenyl]-3-[2-(7-oxo-8H-1,8-naphthyridin-3-yl)ethynyl]benzamide;
   e. 4-methyl-N-[3-[(4-methylpiperazin-1-yl)methyl]-5-(trifluoromethyl)phenyl]-3-[2-(7-oxo-8H-1,8-naphthyridin-3-yl)ethynyl]benzamide;
   f. N-[3,5-bis(trifluoromethyl)phenyl]-4-methyl-3-[2-(7-oxo-8H-1,8-naphthyridin-3-yl)ethynyl]benzamide;
   g. N-[4-methyl-3-[2-(7-oxo-8H-1,8-naphthyridin-3-yl)ethynyl]phenyl]-3,5-bis(trifluoromethyl)benzamide;
   h. 4-methyl-3-[2-(7-oxo-8H-1,8-naphthyridin-3-yl)ethynyl]-N-[3-(trifluoromethyl)phenyl]benzamide;
   i. N-[4-methyl-3-[2-(7-oxo-8H-1,8-naphthyridin-3-yl)ethynyl]phenyl]-3-(trifluoromethyl)benzamide.

3. The compound according to claim 1 or a pharmaceutically acceptable salt thereof, which compound is 4-methyl-N-[4-[(4-methylpiperazin-1-yl)methyl]-3-(trifluoromethyl)phenyl]-3-[2-(7-oxo-8H-1,8-naphthyridin-3-yl)ethynyl]benzamide.

4. A pharmaceutical composition comprising (i) a compound of Formula (I), or an N-oxide or pharmaceutically acceptable salt thereof; and (ii) a pharmaceutically acceptable carrier, wherein the compound of Formula (I) has the structure:

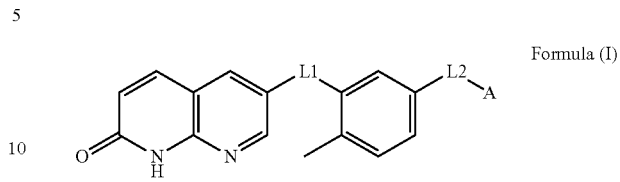

wherein:
L1 is a linker selected from a carbon-carbon triple bond or a carbon-carbon double bond;
L2 is a linker selected from —NHC(O)—, —C(O)NH—; and
A is selected from the group consisting of:

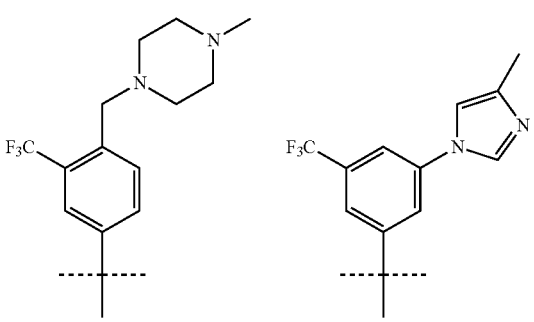

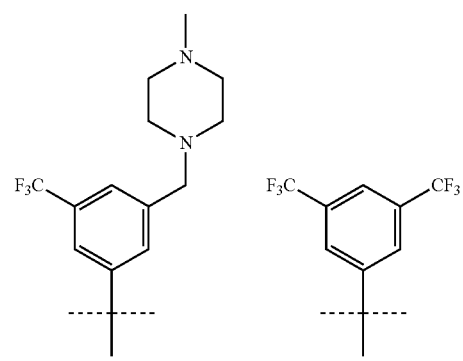

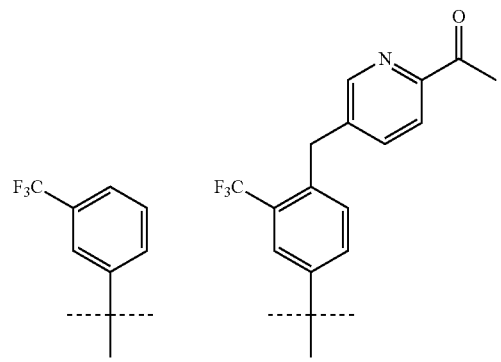

-continued

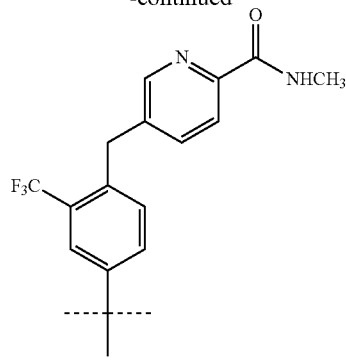

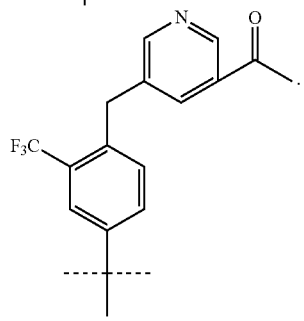

5. A pharmaceutical composition according to claim 4, which pharmaceutical composition comprises (i) 4-methyl-N-[4-[(4-methylpiperazin-1-yl)methyl]-3-(trifluoromethyl)phenyl]-3-[2-(7-oxo-8H-1,8-naphthyridin-3-yl)ethynyl]benzamide or a pharmaceutically acceptable salt thereof; and (ii) a pharmaceutically acceptable carrier.

6. The compound according to claim 1 or an N-oxide or pharmaceutically acceptable salt thereof, which compound is a compound of Formula (Ia):

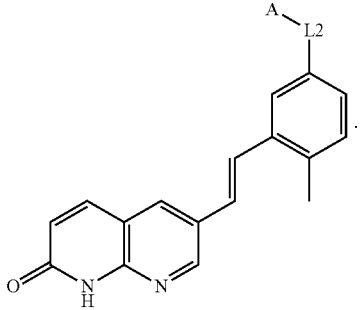

Formula (Ia)

7. The compound according to claim 1 or an N-oxide or pharmaceutically acceptable salt thereof, which compound is a compound of formula (Ib):

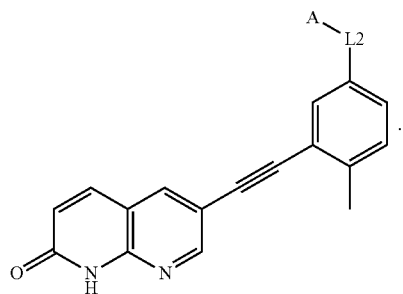

Formula (Ib)

* * * * *